US009611295B2

(12) United States Patent
Li et al.

(10) Patent No.: US 9,611,295 B2
(45) Date of Patent: Apr. 4, 2017

(54) TREATMENT OF IL-17 MEDIATED DISEASE BY BLOCKING SEFIR-SEFIR INTERACTIONS

(71) Applicant: THE CLEVELAND CLINIC FOUNDATION, Cleveland, OH (US)

(72) Inventors: Xiaoxia Li, Cleveland, OH (US); Caini Liu, Cleveland, OH (US); Junpeng Deng, Cleveland, OH (US); Thomas A. Hamilton, Cleveland, OH (US); Jarod Zepp, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/354,608

(22) PCT Filed: Oct. 29, 2012

(86) PCT No.: PCT/US2012/062380
§ 371 (c)(1),
(2) Date: Apr. 28, 2014

(87) PCT Pub. No.: WO2013/063557
PCT Pub. Date: May 2, 2013

(65) Prior Publication Data
US 2015/0158912 A1    Jun. 11, 2015

Related U.S. Application Data

(60) Provisional application No. 61/552,042, filed on Oct. 27, 2011.

(51) Int. Cl.
| | | |
|---|---|---|
| *C07K 14/00* | (2006.01) |
| *C07K 7/08* | (2006.01) |
| *C07K 7/06* | (2006.01) |
| *A61K 38/08* | (2006.01) |
| *A61K 38/10* | (2006.01) |
| *A61K 38/16* | (2006.01) |

(52) U.S. Cl.
CPC ............... *C07K 7/08* (2013.01); *A61K 38/08* (2013.01); *A61K 38/10* (2013.01); *A61K 38/16* (2013.01); *C07K 7/06* (2013.01); *C07K 14/00* (2013.01)

(58) Field of Classification Search
None
See application file for complete search history.

(56) References Cited

FOREIGN PATENT DOCUMENTS

WO    0190358 A2    11/2001
WO    WO 0190358 A2 * 11/2001    ........... C07K 14/715

OTHER PUBLICATIONS

Bogoyevitch, Marie A., et al. "Taking the cell by stealth or storm? Protein transduction domains (PTDs) as versatile vectors for delivery." DNA and cell biology 21.12 (2002): 879-894.

Chang, Seon Hee, Heon Park, and Chen Dong. "Act1 adaptor protein is an immediate and essential signaling component of interleukin-17 receptor." Journal of Biological Chemistry 281.47 (2006): 35603-35607.

Claudio, Estefania, et al. "The adaptor protein CIKS/Act1 is essential for IL-25-mediated allergic airway inflammation." The Journal of Immunology 182.3 (2009): 1617-1630.

Fischer, Peter M., Eberhard Krausz, and David P. Lane. "Cellular delivery of impermeable effector molecules in the form of conjugates with peptides capable of mediating membrane translocation." Bioconjugate chemistry 12.6 (2001): 825-841.

Garcia-Echeverria, C., and Stephan Ruetz. "β-homolysine oligomers: A new class of trojan carriers." Bioorganic & medicinal chemistry letters 13.2 (2003): 247-251.

Leifert, Jens A., and J. Lindsay Whitton. "'Translocatory proteins' and 'protein transduction domains': a critical analysis of their biological effects and the underlying mechanisms." Molecular Therapy 8.1 (2003): 13-20.

Lindsay, Mark A. "Peptide-mediated cell delivery: application in protein target validation." Current opinion in pharmacology 2.5 (2002): 587-594.

Liu, Caini, et al. "Act1, a novel U-box E3 ubiquitin ligase for IL-17R-mediated signalling." Science signaling 2.92 (2011): ra63.

Liu, Caini, et al. "A CC' loop decoy peptide blocks the interaction between Act1 and IL-17RA to attenuate IL-17-and IL-25-induced inflammation." Science signaling 4.197 (2011): ra72.

Maitra, Amarnath, et al. "Distinct functional motifs within the IL-17 receptor regulate signal transduction and target gene expression." Proceedings of the National Academy of Sciences 104.18 (2007): 7506-7511.

Novatchkova, Maria, et al. "The STIR-domain superfamily in signal transduction, development and immunity." Trends in biochemical sciences 28.5 (2003): 226-229.

Qian, Youcun, et al. "The adaptor Act1 is required for interleukin 17-dependent signaling associated with autoimmune and inflammatory disease." Nature immunology 8.3 (2007): 247-256.

Rickel, Erika A., et al. "Identification of functional roles for both IL-17RB and IL-17RA in mediating IL-25-induced activities." The Journal of Immunology 181.6 (2008): 4299-4310.

Roy, Ambrish, Alper Kucukural, and Yang Zhang. "I-TASSER: a unified platform for automated protein structure and function prediction." Nature protocols 5.4 (2010): 725-738.

Swaidani, Shadi, et al. "The critical role of epithelial-derived Act1 in IL-17-and IL-25-mediated pulmonary inflammation." The Journal of Immunology 182.3 (2009): 1631-1640.

(Continued)

*Primary Examiner* — Lianko Garyu
(74) *Attorney, Agent, or Firm* — Tarolli, Sundheim, Covell & Tummino LLP

(57) ABSTRACT

A method of treating an IL-17 mediated disease in a subject by administering to the subject a therapeutically effective amount of a of a cell-permeable decoy peptide that competitively inhibits binding of the SEFIR domain of IL-17R to the SEFIR domain of Act1. In particular, it has been determined that the αC helix region of the SEFIR domain of both IL-17R and Act1 plays an important role in the association of IL-17R and Act1. To facilitate cell permeation, the decoy peptide is preferably conjugated to a protein transduction domain. Examples of IL-17 mediated diseases include various human and animal inflammatory and autoimmune diseases such as asthma.

20 Claims, 12 Drawing Sheets

(56) References Cited

OTHER PUBLICATIONS

Shen, Fang, and Sarah L. Gaffen. "Structure-function relationships in the IL-17 receptor: implications for signal transduction and therapy." Cytokine 41.2 (2008): 92-104.

Toshchakov, Vladimir Y., and Stefanie N. Vogel. "Cell-penetrating TIR BB loop decoy peptides: A novel class of TLR signaling inhibitors and a tool to study topology of TIR-TIR interactions." (2007): 1035-1050.

Toy, Dean, et al. "Cutting edge: interleukin 17 signals through a heteromeric receptor complex." The Journal of Immunology 177.1 (2006): 36-39.

Tung, Ching-Hsuan, and Ralph Weissleder. "Arginine containing peptides as delivery vectors." Advanced drug delivery reviews 55.2 (2003): 281-294.

International Search Report and Written Opinion for PCT/US2012/062380, mailed Mar. 29, 2013, pp. 1-12.

\* cited by examiner

| | |
|---|---|
| miL17RB-SEFIR | LLPLIKVLVVYPS-EICFHHTVCRFTDFLQNYCR--SEVILEKWQKKKIAEMGPVQWLTT |
| hiL17RB-SEFIR | LLPPIKVLVVYPS-EICFHHTICYFTEFLQNHCR--SEVILEKWQKKKIAEMGPVQWLAT |
| miL17RA-SEFIR | ----RKVWIVYSADHPLYVEVVLKFAQFLITACG--TEVALDLLEEQVISEVGVMTWVSR |
| hiL17RA-SEFIR | ----RKVWIIYSADHPLYVDVVLKFAQFLLTACG--TEVALDLLEEQAISEAGVMTWVGR |
| miL17RC-SEFIR | --GSRTALLLHSADGAGYERLVGALASALSQMP---LRVAVDLWSRRELSAHGALAWFHH |
| hiL17RC-SEFIR | -RGRAALLLYSADDSGFERLVGALASALCQLP---LRVAVDLWSRRELSAQGPVAWFHA |
| hActI-SEFIR | ----EELRKVFITYSMDTAMEVVKFVNFLLVNG--FQTAIDIFEDR-IRGIDIIKWMER |
| mActI-SEFIR | ----EELRKVFITYSMDTAMEVVKFVNFLLVNG--FQTAIDIFEDR-IRGIDIIKWMER |
| 2J67-TIR | RNVRFHAFISYSE---HDSLWVKNELIPNLEKEDGSILICLYESYFD-PGKSISENIVS |

| | |
|---|---|
| miL17RB-SEFIR | QKQ----AADKVVFLLPSDVPTLCDSACGHNEG------SARENSQ--DLFPLAFN |
| hiL17RB-SEFIR | QKK---AADKVVFLLSNDVNSVCDGTCGKSEG--------SPSENSQ--DLFPLAFN |
| miL17RA-SEFIR | QKQEMVESNSKIIILCSRGTQAKWKAILGWAEP---AVQLRCDHWKPAG--DLFTAAMN |
| hiL17RA-SEFIR | QKQEMVESNSKIIVLCSRGTRAKWQALLGRGAP----VRLRCDHGKPVG--DLFTAAMN |
| miL17RC-SEFIR | QRRRILQEGGVVILLFSPAAVAQCQQWLQLQTV---------EPGPH---DALAAWLS |
| hiL17RC-SEFIR | QRRQTLQEGGVVVLLFSPGAVALCSEWLQDGVS-------GPGAHGPH--DAFRASLS |
| hActI-SEFIR | YLR----DKTVMIIVAISPKYKQDVEGAESQLD-----------EDEH--GLHTKYIH |
| mActI-SEFIR | YLR----DKTVMIIVAISPKYKQDVEGAESQLD-----------EDEH--GLHTKYIH |
| 2J67-TIR | FIE----KSYKSIFVLS----------------------PNFVQNEWCHYEF |

| | |
|---|---|
| miL17RB-SEFIR | -LFCSDFSSQTHLHKYLVVYLGGADLKGD-----YNALS-VCPQYHLMK--------- |
| hiL17RB-SEFIR | -LFCSDLRSQIHLHKYVVVYFREIDTKDD-----YNALS-VCPKYHLMK--------- |
| miL17RA-SEFIR | -MILPDFKRPACFGTYVVCYFSGICSERD-----VPDLFNITSRYPLMDRFEEVYFRIQ |
| hiL17RA-SEFIR | -MILPDFKRPACFGTYVVCYFSEVSCDGD-----VPDLFGAAPRYPLMDRFEEVYFRIQ |
| miL17RC-SEFIR | -CVLPDFLQGRATGRYVGVYFDGLLHPDS-----VPSPFRVAPLFSLPTQLPAFLDALQ |
| hiL17RC-SEFIR | -CVLPDFLQGRAPGSYVGACFDRLLHPDA-----VPALFRTVPVFTLPSQLPDFLGALQ |
| hActI-SEFIR | RMMQIEFIKQGSMNFRFIPVLFPNAKKEH-----VPTWLQNTHVYSWPK--------- |
| mActI-SEFIR | RMMQIEFISQGSMNFRFIPVLFPNAKKEH-----VPTWLQNTHVYSWPK--------- |
| 2J67-TIR | -YFAHHNLFHENSDHIILILLEPIPFYCIPTRYHKLKALLEKKAYLEWPKDRRKCGL--- |

| | |
|---|---|
| miL17RB-SEFIR | -DATAFHTELLKATQ---------------------- |
| hiL17RB-SEFIR | -DATAFCAELLHVKQ---------------------- |
| miL17RA-SEFIR | DLEMFEPGRMHRVGE---------------------- |
| hiL17RA-SEFIR | DLEMFQPGRMHHVRE---------------------- |
| miL17RC-SEFIR | GGCSTSAGRPADRVE---------------------- |
| hiL17RC-SEFIR | QPRAPRSGRLQERAE---------------------- |
| hActI-SEFIR | -NKKNILLRLLREEE---------------------- |
| mActI-SEFIR | -NKKNILLRLLREEE---------------------- |
| 2J67-TIR | -FWANLRAAIN-------------------------- |

FIG. 7

TREATMENT OF IL-17 MEDIATED DISEASE BY BLOCKING SEFIR-SEFIR INTERACTIONS

CONTINUING APPLICATION DATA

This application claims the benefit of U.S. Provisional Application Ser. No. 61/552,042, filed Oct. 27, 2011, which is incorporated by reference herein.

GOVERNMENT FUNDING

This invention was made with government support under HL098935 and NS071996 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Sep. 16, 2014, is named CCF-020904US-PCT SL.txt and is 25,025 bytes in size.

BACKGROUND

Homology-based cloning has revealed six members of the family of interleukin-17 (IL-17) cytokines, which are termed IL-17A to IL-17F. IL-17A, which is produced by the T helper 17 (TH17) subset of CD4+ T cells, is the prototypic IL-17 family member, and it exerts its actions either as a homodimer or as a heterodimer with IL-17F. IL-17 is required for host defense against extracellular microorganisms and is also involved in the pathogenesis of various human and animal autoimmune diseases, such as rheumatoid arthritis, multiple sclerosis (MS), experimental autoimmune encephalomyelitis (EAE, a mouse model of MS), and allergen-induced pulmonary inflammation. The main function of IL-17 is to coordinate local tissue inflammation through the increased production of proinflammatory and neutrophil mobilizing cytokines and chemokines. IL-17 promotes the accumulation of neutrophils in the bronchoalveolar lavage (BAL) fluid of rats and mice. Increased concentrations of IL-17 are found in the lungs and blood of allergic asthma patients and are correlated with the severity of asthma. Kolls et al., Am. J. Respir. Cell Mol. Biol. 28, 9-11 (2003).

Another well-characterized IL-17 family member is IL-17E (also referred to as IL-25), which is the most divergent member of the IL-17 family. IL-25 is produced by airway epithelial cells in response to allergens and by mouse CD4+ T cells that have a $T_H2$ profile, as well as by the human eosinophils and basophils, which are innate effector cells. IL-25 plays a critical role in the initiation and propagation of the $T_H2$-type immune response. Wang et al., J. Exp. Med. 204, 1837-1847 (2007). Transgenic expression of IL-25 in mice as well as recombinant IL-25 induces $T_H2$-type immunity and leads to increases in the concentrations of the $T_H2$-type cytokines IL-4, IL-5, and IL-13, as well as increased eosinophilia and serum concentrations of immunoglobulin E (IgE). Tamachi et al., J. Allergy Clin. Immunol. 118, 606-614 (2006). In IL-25-deficient mice, expulsion of helminth parasites is delayed, indicating an impairment of the $T_H2$-type immune response. Furthermore, endogenous IL-25 is critical in allergen-induced pulmonary airway hyperreactivity (AHR) and inflammation in a mouse model of asthma. Increased concentrations of IL-25 are detected in asthmatic lung tissues compared to those found in normal tissue, highlighting a role for IL-25 in allergic pulmonary inflammation. Angkasekwinai et al., J. Exp. Med. 204, 1509-1517 (2007).

Given studies that have defined critical roles for IL-17 in autoimmune inflammatory responses, a mechanistic understanding of IL-17-mediated signaling is required to develop new and improved therapeutics for the treatment of inflammatory diseases. IL-17R (IL-17RA and IL-17RC) and IL-25R (IL-17RB and IL-17RA) belong to the recently defined family of SEFIR proteins, which are characterized by the presence of a conserved SEFIR domain in their cytoplasmic regions. Novatchkova et al., Trends Biochem. Sci. 28, 226-229 (2003). SEFIR domains share limited homology with Toll-IL-1 receptor (TIR) domains of Toll-like receptors (TLRs) and IL-1Rs, and SEFIR and TIR domains together constitute the (SEFIR/TIR) domain superfamily. Because TIR domains mediate TIR-TIR homotypic interactions, it was thought that the SEFIR domain might also mediate protein-protein interactions.

The inventors and others have reported that the adaptor protein nuclear factor kB (NF-kB) activator 1 (Act1, encoded by the gene TRAF3IP2), which is also known as CIKS [connection to inhibitor of kB kinase (IKK) and stress-activated protein kinase (SAPK)/c-Jun N-terminal kinase (JNK)], is a key component in IL-17 signaling. Claudio et al., J. Immunol. 182, 1617-1630 (2009). Qian et al., Nat. Immunol. 8, 247-256 (2007). Act1 also contains a SEFIR domain and is a member of the SEFIR protein family. Upon stimulation with IL-17, Act1 is recruited to the IL-17R and the IL-25R through SEFIR-SEFIR domain interactions, which is followed by the recruitment of transforming growth factor β-activated kinase 1 (TAK1) and tumor necrosis factor (TNF) receptor-associated factor 6 (TRAF6), which mediate downstream activation of NF-κB. Chang et al., J. Biol. Chem. 281,35603-35607 (2006). In addition, Act1 contains a helix-loop-helix domain at its N terminus, two TRAF-binding sites, and a U-box-like region N-terminal to the SEFIR domain. The inventors found that Act1 functions as an E3 ubiquitin ligase through its U-box-like region and that this activity is essential for IL-17-mediated signaling pathways. Liu et al., Sci. Signal. 2, ra63 (2009). Consistent with its role in signaling, Act1 is required for IL-17-dependent expression of genes encoding proinflammatory factors and for pulmonary neutrophilia, whereas Act1 deficiency abolishes IL-25-induced production of $T_H2$-type cytokines and IL-25-dependent pulmonary eosinophilia. Swaidani et al., J. Immunol. 182, 1631-1640 (2009). However, although heterodimeric interactions between the SEFIR domain of Act1 and that of the IL-17R are known, the molecular details of SEFIR-SEFIR interactions still remain unclear.

SUMMARY

As it is established that IL-17 is a key modulator of immune and inflammatory diseases, it would be desirable to identify IL-17 blockers, i.e., substances capable of blocking or interrupting the activity of IL-17, for use in anti-inflammatory compositions in the treatment of, e.g., asthma, rheumatoid arthritis or multiple sclerosis. Such compositions may also prove to be more advantageous over presently available NSAIDS, steroid based anti-inflammatory drugs and cytotoxic drugs which often have severe side effects with the continued usage that is required for chronic inflammatory diseases.

The inventors have developed cell-permeable decoy peptides that suppress IL-17 signaling. Whereas previous studies have shown that the BB' loop is required for TIR-TIR domain interactions, the inventors found that deletion of the region containing the BB' loop did not affect the interaction between Act1 and IL-17RA. Indeed, an additional helix ($C_{ins}$) is inserted between the third strand (C) and the third helix (C') in the SEFIR domain. A distinct interaction interface (the CC' loop) within the Act1 SEFIR domain was defined by mutagenesis and decoy peptide approaches. It was initially shown that the CC' loop in the Act1 SEFIR domain was required for the interaction of Act1 with IL-17RA (the common subunit of IL-17R and IL-25R), as well as for IL-17-dependent signaling. While later work re-characterized the secondary structure of this region, the amino acid sequences involved remained the same. A cell-permeable decoy peptide designed from the CC' loop of the Act1 SEFIR domain inhibited IL-17-mediated signaling and inflammatory gene expression in cultured cells. The decoy peptide also inhibited IL-17-and IL-25-induced pulmonary inflammation in mice, initially indicating that the CC' loop was a promising therapeutic target region within Act1 for the treatment of IL-17-associated inflammatory diseases.

The inventors also determined the structure of the first SEFIR domain from IL-17RB at 1.8 Å resolution. SEFIR displays a five stranded parallel β-sheet that is wrapped by six helices. Mutagenesis carried out on IL-17RB identified helix αC as critical for its interaction with Act1 and IL-25 signaling. Helix αC is also conserved in IL-17RA and IL-17RC, suggesting this helix as a common structural signature for heterotypic SEFIR-SERIR association. Reassessment of previously reported key functional residues in Act1 also pointed to the importance of helix αC, rather than the CC' loop, in Act1. The inventors have also shown that helix αB' is important for homodimerization of Act1. The data suggest a dual ligand-binding model for SEFIR domain, with distinct structural motifs participating in either homotypic or heterotypic interactions.

Accordingly, in one aspect, the present invention provides a method of treating an IL-17 mediated disease in a subject that includes administering to the subject a therapeutically effective amount of a cell-permeable decoy peptide that competitively inhibits binding of the SEFIR domain of IL-17R to the SEFIR domain of Act1. In some embodiments, the decoy peptide consists of less than about 50 amino acids. In a further embodiment, the decoy peptide comprises an amino acid sequence substantially homologous to at least a portion of the amino acid sequence of the αC helix region of the SEFIR domain of Act1 or at least a portion of the αC helix region of the SEFIR domain of IL-17R. In additional embodiments, the decoy peptide can include a protein transduction domain to facilitate cell permeation.

The IL-17 mediated disease can be an inflammatory disease or an autoimmune disease. More specifically, the IL-17 mediated disease can be an inflammatory disease selected from the group consisting of asthma, inflammatory bowel disease, multiple sclerosis, experimental autoimmune encephalomyelitis, and allergen-induced pulmonary inflammation. Alternately, the IL-17 mediated disease is an autoimmune disease selected from the group consisting of systemic lupus erythematosus, rheumatoid arthritis, allograft rejection, drug-induced lupus and psoriasis.

Another aspect of the invention relates to the isolated decoy peptides themselves. In one embodiment, the decoy peptide comprises an isolated peptide comprising an amino acid sequence substantially homologous to at least a portion of the amino acid sequence of the αC helix region of the SEFIR domain of Act1 and further comprising the amino acid sequence HGLHXKY (SEQ ID NO: 1). In another embodiment, the decoy peptide comprises an isolated peptide comprising amino acid sequence substantially homologous to at least a portion of the amino acid sequence of the αC helix region of the SEFIR domain of IL-17R and further comprising the amino acid sequence DLFXXA (SEQ ID NO:2).

BRIEF DESCRIPTION OF THE FIGURES

FIG. 1A provides a schematic of wild-type (WT) mAct1 and mAct1 SEFIR deletion mutants. FIG. 1B provides Western Blot results of an experiment in which HeLa cells were transiently cotransfected with plasmids encoding FLAG-tagged mouse Act1 or its deletion mutants together with plasmid encoding V5-tagged IL-17RA. Lysates of transfected cells were subjected to immunoprecipation (IP) with antibody against the V5 tag, after which they were analyzed by Western blotting (IB) with antibodies against FLAG and V5. WCL, whole-cell lysate. FIG. 1C provides bar graphs of the results of experiments in which Act1$^{-/-}$ MEFs expressing IL-17RB were reconstituted with either empty vector, FLAG-tagged mAct1, or FLAG-tagged deletion mutants of mAct1 by retroviral infection, after which they were treated with IL-17 (50 ng/ml) or IL-25 (100 ng/ml) for 3 hours. The abundances of Cxcl1 and Il13 messenger RNAs (mRNAs) were measured by real-time RT-PCR and the results are expressed as fold-induction calculated as a ratio of the abundance of a given mRNA in the treated sample to that in the untreated sample. The experiment was repeated five times and the data are shown as the mean±the standard error of the mean (SEM). All other experiments were performed three times, with representative blots shown.

FIGS. 3A and B provide bar graphs showing the results of experiments in which Act1$^{-/-}$ MEFs expressing IL-17RB were reconstituted with empty vector, FLAG-tagged mAct1, or (A) FLAG-tagged 3-AA CC' loop mutants or (B) single-AA CC' loop mutants, as indicated, by retroviral infection, after which cells were treated with IL-17 or IL-25. The abundances of Cxcl1 and Il13 mRNAs were measured by real-time RT-PCR, and the fold-induction in mRNA amounts was calculated as a ratio of the amount of mRNA in the treated sample compared to that in the untreated sample. Data are the means±SEMs from three experiments. FIG. 3C shows the Western Blot results of experiments in which HeLa cells were transiently cotransfected with plasmids encoding FLAG-tagged mAct1 or the indicated single-AA point mutants of Act1 together with plasmid encoding V5-tagged IL-17RA. Cell lysates were subjected to immunoprecipitation with antibody against V5, after which they were analyzed by Western blotting with antibodies against the FLAG and V5 tags. FIG. 3D shows the Western Blot results of experiments in which HeLa cells were transiently cotransfected with plasmids encoding FLAG-tagged mAct1 or the indicated single-AA point mutants of Act1 together with plasmid encoding V5-tagged mAct1. Cell lysates were subjected to immunoprecipitation with antibody against the V5 tag, after which they were analyzed by Western blotting with antibodies against the FLAG and V5 tags. Data in (C) and (D) are representative of three experiments.

FIG. 4A provides sequences of Antennapedia homeodomain (Antp) (SEQ ID NO: 11)and decoy peptides (SEQ ID NOS 23-25 and 17, respectively, in order of appearance) with the Antp sequence underlined. FIG. 4B provides flow cytometry results based on experiments in which MEFs expressing IL-17RB were incubated for 2 or 24 hours with the indicated FITC-tagged peptides (200 μM) and were then analyzed by flow cytometry. Data show the analysis of FITC-positive cells from untreated (left peak) and FITC-tagged peptide-treated (right peak) samples. The percentages of FITC-positive cells in the treated samples are shown. FIG. 4C provides Western blot results of experiments in which HeLa cells were cotransfected with plasmids encoding FLAG-tagged mAct1 and V5-tagged IL-17RA and were cultured for 24 hours, after which they were incubated for 24 hours with the indicated peptides (200 μM). IL-17RA was immunoprecipitated from the samples with antibody against the V5 tag, and samples were then subjected to Western blotting analysis with the indicated antibodies. FIG. 4D provides Western blot results of experiments in which MEFs expressing IL-17RB were incubated with the indicated peptides (200 μM) for 24 hours after which they were treated with IL-17 or IL-25 and then analyzed by Western blotting with the indicated antibodies. FIG. 4E provides bar graphs showing the results of experiments in which MEFs expressing IL-17RB were incubated with the indicated peptides (200 μM) for 24 hours, after which they were treated with IL-17 or IL-25 for 3 hours. The abundances of Cxcl1 and Il13 mRNAs were then measured by real-time RT-PCR. Data shown are means±SEM from three individual experiments. *P<0.05 (difference between samples treated with DMSO or the CC' loop peptide). Representative blots are shown from three individual experiments.

FIG. 5A shows that mice pretreated with the CC' peptide showed reduced accumulation of neutrophils in BAL fluid after intranasal administration of IL-17 compared to that in BAL fluid from mice pretreated with the scrambled peptide. FIG. 5B shows that IL-17-associated cytokines MCP-1 and GM-CSF were measured by enzyme-linked immunosorbent assay (ELISA) analysis of the BAL from IL-17-treated mice. FIG. 5C shows the H&E staining of lung tissue from IL-17-treated mice showed that IL-17-induced airway recruitment of granulocytes, was reduced in mice pretreated with the CC' loop decoy peptide compared to that in mice pretreated with the scrambled peptide or DMSO. FIG. 5D shows the Real-time RT-PCR analysis of gene expression in lung tissue from IL-17-treated mice. FIG. 5E shows that mice pretreated with the CC' decoy peptide showed reduced accumulation of eosinophils in the BAL after intranasal administration of IL-25 compared to that in the BAL from mice pretreated with the scrambled peptide. FIG. 5F shows the ELISA analysis of the IL-25-associated cytokines IL-5 and IL-13 in the BAL of IL-25-treated mice. FIG. 5G shows H&E and PAS staining of lung tissue from IL-25-treated mice showed that IL-25-induced airway recruitment of granulocytes, predominantly eosinophils, as well as mucin production, as determined by PAS staining, were reduced in mice pretreated with the CC' loop decoy peptide compared to that in mice pretreated with the scrambled peptide or DMSO. FIG. 5H shows real-time RT-PCR analysis of gene expression in lung tissue from IL-25-treated mice. All experiments were performed three times. *P<0.05.

FIG. 6A provides computational modeling of the SEFIR domains of IL-17RA (SEQ ID NO: 26), IL-17RB (SEQ ID NO: 27), and IL-17RC (SEQ ID NO: 28)in comparison with the SEFIR domain of Act1. (SEQ ID NO: 22)The critical structures are the BB' loop; the $C_{ins}$ helix; and the CC' loop. FIG. 6B shows Western blot results of experiments in which HeLa cells were transiently cotransfected with plasmids encoding V5-tagged IL-17RA or its D-BB' or D-CC' mutants together with plasmid encoding FLAG-tagged mAct1. Cell lysates were subjected to immunoprecipitation with antibody against the V5 tag, after which they were analyzed by Western blotting with antibodies against the FLAG and V5 tags. FIG. 6C shows Western blot results of experiments in which HeLa cells were transiently cotransfected with plasmid encoding V5-tagged IL-17RB or its D-BB' or D-CC' mutants together with plasmid encoding FLAG-tagged mAct1. Cell lysates were subjected to immunoprecipitation with antibody against the V5 tag, after which they were analyzed by Western blotting with antibodies against the FLAG and V5 tags. Blots shown are representative of three independent experiments.

FIG. 7 provides a multiple sequence alignment (SEQ ID NOS 29-37, respectively, in order of appearance) of selected SEFIR and TIR domains. Depicted are IL-17RA, RB, RCE and Act1 from mouse and human, and human TLR10-TIR (PDB 2j67).

FIG. 8A shows the overall structure. The secondary structures are labeled and shown in rainbow colors, with N-terminus colored in blue and C-terminus in red. The CC' segment (residues 396-416) is disordered and not visible from the current structure. The CC' segment was modeled by using FALC-Loop server and optimized manually with program Coot to remove stereo clashes, as shown in salmon color. FIG. 8B provides a 2mFo-DFc electron density map covering a section of the structure containing the DD' loop (contoured at 1.0σ level). The DD' loop is well defined, which embraces a space filled with hydrophobic residues that are well defined from the electron density map. FIG. 8C shows the Helix αB' of IL-17RB-SEFIR is tethered to helices αB and αC via hydrophobic interactions and hydrogen bond. FIG. 8D shows that IL-17RB doesn't contain TRAF6 binding motif. The two residues P334 and F341 in the putative TRAF6 binding motif (VYPSEICF (SEQ ID NO: 3), shown in sticks with key residues colored in red) are completely buried inside the SEFIR structure (the surface of the rest of the structure is shown in green), not possible for interacting with other proteins. The proline and phenylalanine residues at corresponding positions in the canonical TRAF6 motif are critical for binding.

FIG. 9A shows IL-17RB-deficient MEFs were reconstituted with empty vector, Myc-tagged mouse RB mutants as indicated, by retroviral infection, after which cells were treated with IL-25 for 10 min, followed by immunoprecipitation with antibody against Myc and Western analysis with indicated antibodies. FIG. 9B shows the same cells (as indicated in panel A) were treated by IL-25 for 3 hours. The abundances of il-13 mRNAs were measured by real-time RT-PCR, and the fold-induction in mRNA amounts was calculated as a ratio of the amount of mRNA in the treated sample compared to that in the untreated sample. Data are the means±SEMs from three experiments. FIG. 9C shows HeLa cells were transiently cotransfected with plasmids encoding V5-tagged mAct1 and FLAG-tagged Act1 or its αB' deletion mutant together with plasmid encoding V5-tagged mAct1. Cell lysates were subjected to immunoprecipitation with antibody against V5 tag. FIG. 9D shows Act1-deficeint MEFs were reconstituted with empty vector, FLAG-tagged mAct1, or its αB' deletion mutant by retroviral infection, after which cells were treated with IL-25 for 3 hours. The abundances of il-13 mRNAs were measured by real-time RT-PCR, and the fold induction in mRNA amounts was calculated as a ratio of the amount of mRNA in the treated sample compared to that in the untreated sample. Data are the means±SEM from three experiments. *P<0.05 (difference from WT).

FIG. 10A provides an SPR analysis of the binding of the Act1-SEFIR to the IL-17RB-SEFIR domain. Purified Act1-SEFIR (0.25 to 4 μM) and bovine serum albumin (BSA, 4 μM) were injected over the surface to which WT IL-17RB-SEFIR or IL-17RB-SEFIR-M (K364A, K367A, K368A and K369A quadruple mutant) was immobilized. Binding signal is recorded as resonance units (RU). FIG. 10B provides a model of heterodimer of Act1-SEFIR and IL-17RB-SEFIR domains. Act1-SEFIR structure was modeled by SWISS-Model interface, using the crystal structure of IL-17RB-SEFIR as template. Subsequent docking of Act1-SEFIR: IL-17RB-SEFIR was carried out with HADDOCK server. Notice the helices αB' (red) from both Act1-SEFIR and IL-17RB-SEFIR are exposed and not involved in the heterodimerization. FIG. 10C shows a IL-17RB-SEFIR crystal structure as electropotential surface, while residues on Act1-SEFIR are shown as sticks (yellow ones on αC and magenta ones on αB). The contact residues from Act1-SEFIR and IL-17RB-SEFIR are labeled in black and blue, respectively. FIG. 10D shows significant conformational changes between the SEFIR and TIR domains. The SEFIR structure is shown in yellow and its DD'-loop in orange. The structure of the TIR domain from TLR10 is shown in blue and its DD' loop in red. The DD'-loop of SEFIR shifted by more than 10 Å, with respect to that in the TIR.

DETAILED DESCRIPTION

Figure 1:
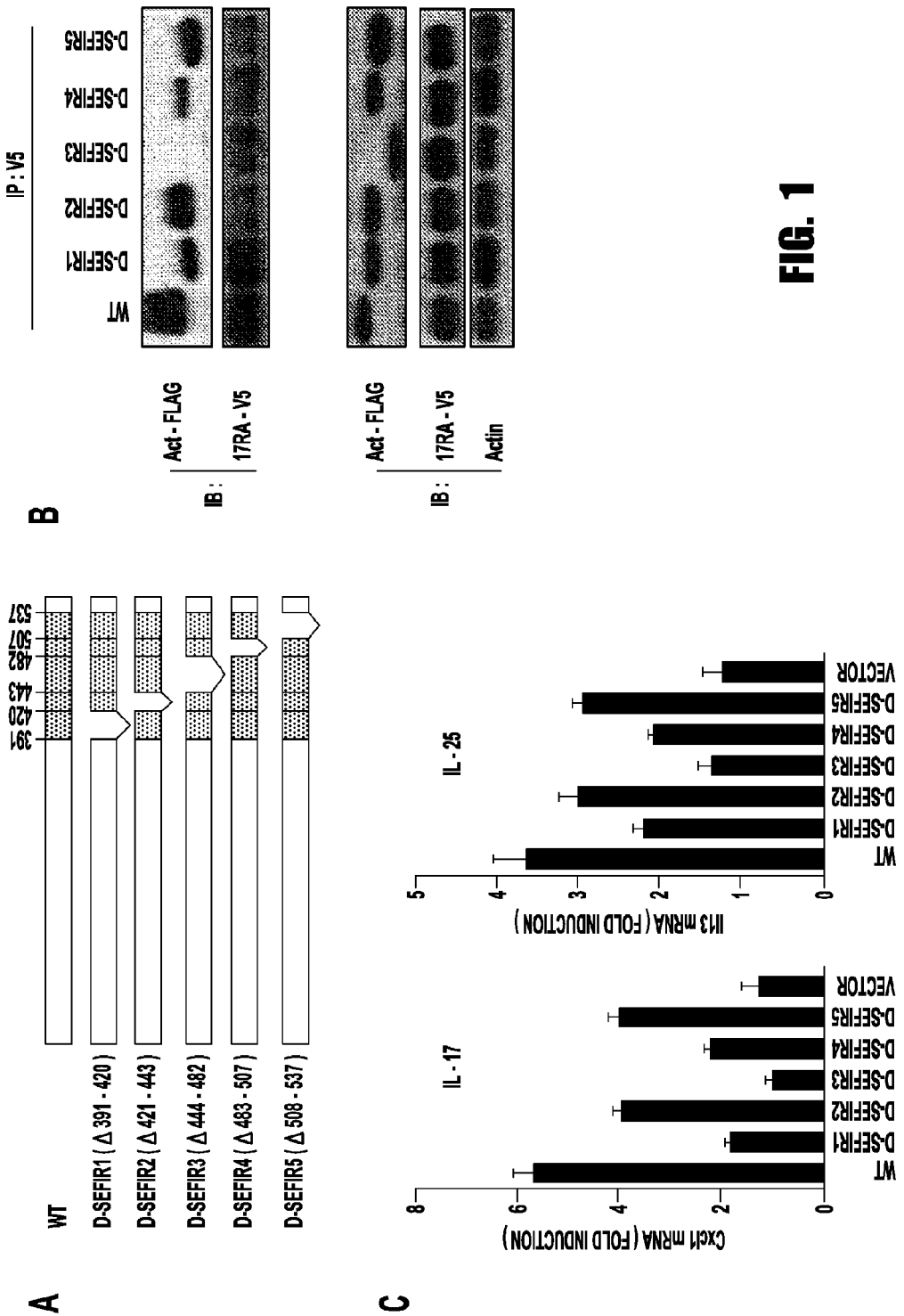
FIG. 1 provides graphical data showing that The SEFIR3 region is critical for the interaction between the Act1 SEFIR domain and IL-17RA.

Unless otherwise defined, all technical and scientific terms used herein have the same meaning as commonly understood by one of ordinary skill in the art to which this application pertains. Although methods and materials similar or equivalent to those described herein can be used in the practice or testing of the exemplary embodiments, suitable methods and materials are described below. In case of conflict, the present specification, including definitions, will control. In addition, the materials, methods, and examples are illustrative only and not intended to be limiting.

The terminology as set forth herein is for description of the embodiments only and should not be construed as limiting the application as a whole. Unless otherwise specified, "a," "an," "the," and "at least one" are used interchangeably. Furthermore, as used in the description of the application and the appended claims, the singular forms "a", "an", and "the" are inclusive of their plural forms, unless contraindicated by the context surrounding such. Furthermore, the recitation of numerical ranges by endpoints includes all of the numbers subsumed within that range (e.g., 1 to 5 includes 1, 1.5, 2, 2.75, 3, 3.80, 4, 5, etc.).

The term "isolated" means that the material is removed from its original environment (e.g., the natural environment if it is naturally occurring) or is synthetically derived. For example, a naturally-occurring polypeptide present in a living animal is not isolated, but the same polypeptide, separated from some or all of the coexisting materials in the natural system, is isolated. Such a polypeptide could be part of a composition, and still be isolated in the composition, and not be a part of its natural environment.

Decoy Peptides

In one aspect, the invention provides a method of treating an interleukin-17 (IL-17) mediated disease in a subject by administering to the subject a therapeutically effective amount of a cell-permeable decoy peptide that competitively inhibits binding of the SEFIR domain of IL-17R to the SEFIR domain of Act1. Preferably, the decoy peptide comprises an amino acid sequence substantially homologous to the amino acid sequence of the αC helix region of the SEFIR domain of Act1 or the αC helix region of the SEFIR domain of IL-17R. In different embodiments, the IL-17 mediating the disease can be one or more various specific subtypes of IL-17. For example, the IL-17 can be one or more of IL-17A, IL-17B, IL-17C, IL-17E (i.e., IL-25), or IL-17F. In addition, IL-17 includes any substantially homologous new subtypes of IL-17 that may be identified in the future.

The term "decoy peptide," as used herein, refers to peptides that are substantially homologous to a portion of the SEFIR domain region of either IL-17R or Act1. As a result of this similarity, decoy peptides can interfere with the regular interaction between. IL-17R and Act1, and thereby act as a "decoy" for the normal substrate of these proteins. Because the interaction of IL-17R and Act1 is necessary for IL-17 activity, the decoy peptides of the present invention are capable of inhibiting IL-17 activity.

The decoy peptides competitively inhibit binding of the SEFIR domain of IL-17R to the SEFIR domain of Act1. By competitive inhibition, it is meant that the decoy peptides occupy at least a portion of the SEFIR domain of either IL-17R or Act1, thereby "competing" with the binding of the natural substrate (i.e., either IL-17R or Act1). Depending on the amount of decoy peptide present, the inhibition can either be essentially complete (i.e., about 100%) or partial (i.e., any percentage less than 100%, such as 90% or 50%).

As described herein, portions of the SEFIR domain of both the IL-17 receptor and Act1 have been identified that are involved in the interaction between these proteins. Accordingly, in one embodiment, the decoy peptide comprises an amino acid sequence substantially homologous to an amino acid sequence within the SEFIR domain of Act1. The sequences described herein are murine sequence of IL-17R and Act1. However, there is substantial homology between the murine amino acid sequence and the human amino acid sequences for the IL-17 receptor and Act1. See FIG. 7, which shows that there is substantial homology between the human and murine sequences for the SEFIR domain of human and murine IL-17RA, IL-17RB, and IL-17RC, as well as the SEFIR domain of Act1. Accordingly the present invention also encompasses sequences from the SEFIR domains of human IL-17R and Act1. Furthermore, it is known that there is substantial homology between SEFIR domains of IL-17R and Act1 of other mammalian species, and peptide decoys based on these other sequences are also encompassed by the invention.

Figure 2:
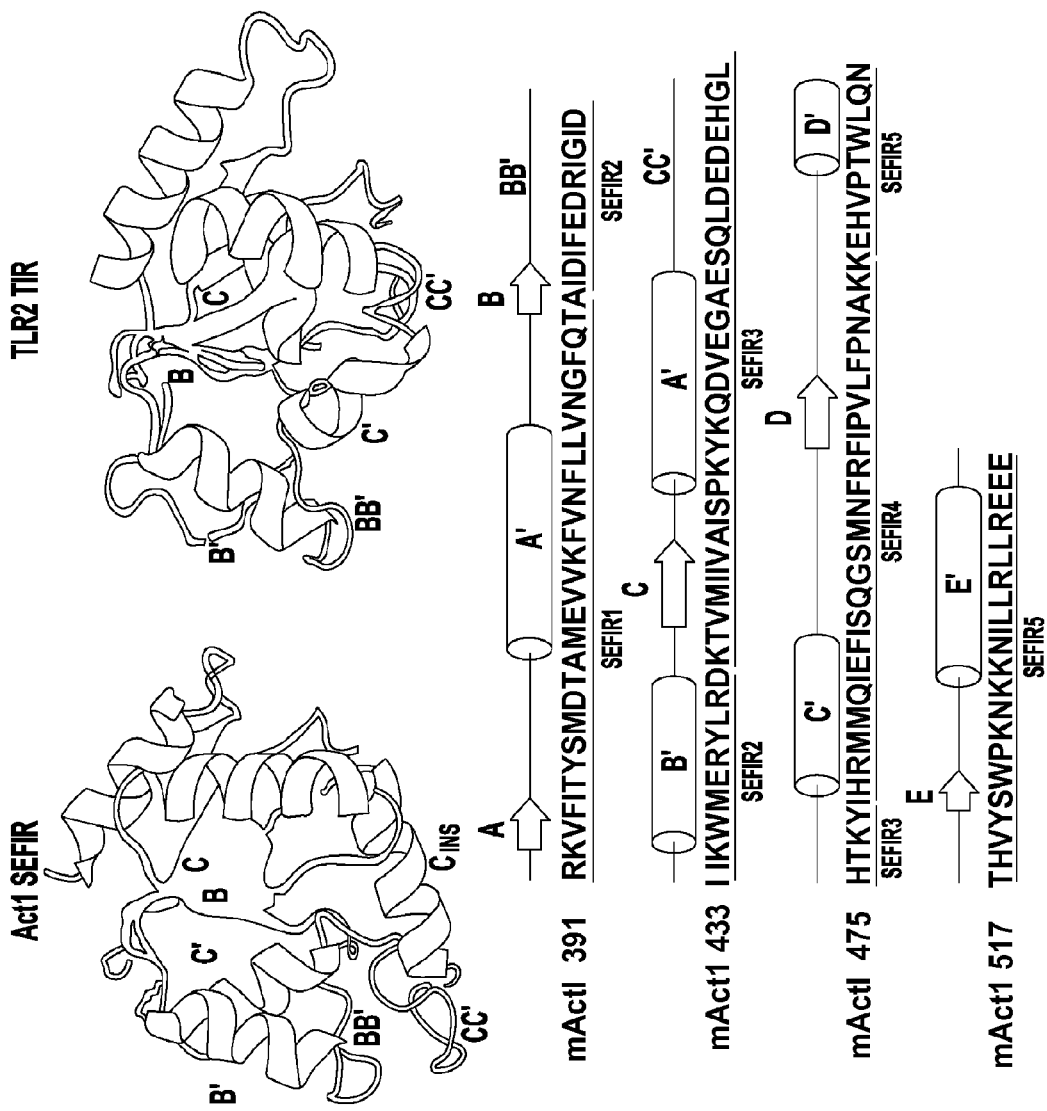
FIG. 2 shows that a CC' loop peptide (SEQ ID NO: 22) corresponding to a region from SEFIR3 that binds directly to IL-17RA. Computational modeling of the SEFIR domain of mAct1 with I-Tasser in comparison to the TIR domain of TLR2 is shown at the top of the figure. The SEFIR domain of Act1 consists of five-stranded β-sheets (A to D) and of five roughly parallel α-helices (A', B', C', $C_{ins}$ and C', D', and E') interconnected by loops. The amino acid sequence of the SEFIR domain of mAct1 is shown below the structures together with the modeled secondary structure.

The SEFIR domain of murine Act1 consists of the amino acid sequence SEQ ID NO: 22, shown in FIG. 2, which includes amino acid residues R391 to E537 of mAct1. The SEFIR domain of Act1 includes five different regions, designated SEFIR1 ($R^{391}$ to $A^{420}$), SEFIR2 ($I^{421}$ to $D^{443}$), SEFIR3 ($K^{444}$ to $M^{482}$), SEFIR4 ($M^{483}$ to $K^{507}$), and SEFIR5 ($E^{508}$ to $E^{537}$). In additional embodiments of the invention, the decoy peptide comprises an amino acid sequence from a portion of the SEFIR3 region, or the decoy peptide comprises an amino acid sequence substantially homologous to at least a portion of the αC helix region of the SEFIR domain of Act1.

Studies by the inventors have shown that some amino acids are particular important for the interaction between the SEFIR domains of Act1 and IL-17R. Accordingly, additional embodiments include specific amino acid sequences within the αC helix region of the SEFIR domain of Act1. Thus, in one embodiment, the decoy peptide comprises the amino acid sequence HGLHXKY (SEQ ID NO: 1), wherein X can be any amino acid. The standard amino acids and their one and three letter abbreviations are known to those skilled in the art. In further embodiments, the decoy peptide comprises the amino acid sequence HGLHTKY (SEQ ID NO: 4), or the amino acid sequence LDEDEHGLHTKY (SEQ ID NO: 5).

In another embodiment, the decoy peptide comprises an amino acid sequence substantially homologous to at least a portion of the amino acid sequence within the SEFIR domain of IL-17R. It should be noted that IL-17R, as used herein, encompasses the various subtypes of IL-17R, such as IL-17RA, IL-17RB, IL-17RC, IL-17RD, and IL-17RE (i.e., IL-25R). The sequences for the murine and human SEFIR domains of IL-17R are shown in FIG. 7. Additional embodiments include specific amino acid sequences within the αC helix region of the SEFIR domain of IL-17R. Thus, in one embodiment, the decoy peptide comprises the amino acid sequence DLFXXA (SEQ ID NO: 2), in which X can be any amino acid, while in another embodiment the decoy peptide comprises the amino acid sequence QDLFPLA (mIL-17RB and hIL-17RB, SEQ ID NO: 6), GDLFTAA (mIL-17RA and hIL-17RA, SEQ ID NO: 7), HDALAAW (mIL-17RC, SEQ ID NO: 8), and HDAFRASLS (hRC, SEQ ID NO: 9).

Embodiments of the invention refer to peptides that are substantially homologous to at least a portion of the amino acid sequence within the SEFIR domains of IL-17R or Act1. The term "a portion," as used herein, refers to an amino acid sequence within the SEFIR domains of IL-17R or Act1 that includes at least 4 amino acids. In further embodiments, a portion refers to an amino acid sequence that is at least 6 amino acids in length, an amino acid sequence that is at least 8 amino acids in length, or an amino acid sequence that is at least 10 amino acids in length. The peptide decoys therefore consist of at least 4, 6, 8, or 10 amino acids. Likewise, the peptide decoys described herein have a maximum size. The maximum size of the peptide decoy relates to the overall size of the peptide, and includes any additional sequences linked to the peptide, such as a protein transduction domain. In some embodiments, the peptide decoy has a maximum size of less than about 200 amino acids, while in other embodiments the peptide decoy has a maximum size of less than about 100 amino acids. In other embodiments, the peptide decoy has a maximum size of less than about 75 amino acids, less than about 50 amino acids, less than about 40 amino acids, or less than about 30 amino acids.

As used herein, the term "polypeptide" refers to an oligopeptide, peptide, or protein sequence, or to a fragment, portion, or subunit of any of these, and to naturally occurring or synthetic molecules. The term "polypeptide" also includes amino acids joined to each other by peptide bonds or modified peptide bonds, i.e., peptide isosteres, and may contain any type of modified amino acids. The term "polypeptide" also includes peptides and polypeptide fragments, motifs and the like, glycosylated polypeptides, all "mimetic" and "peptidomimetic" polypeptide forms, and retro-inversion peptides (also referred to as all-D-retro or retro-enantio peptides).

By "homologs" is meant the corresponding peptides from IL-17R or Act1 of other mammalian species that are substantially homologous at the overall protein (i.e., mature protein) level to human or murine IL-17R or Act1, so long as such homologous peptides retain their respective known activities. Various levels of homology, from 55% to 99%, are described herein.

By "analogs" is meant peptides which differ by one or more amino acid alterations, which alterations, e.g., substitutions, additions or deletions of amino acid residues, do not abolish the properties of the relevant peptides, such as their ability to associate with IL-17R or Act1. An analog may comprise a peptide having a substantially identical amino acid sequence to a peptide provided herein and in which one or more amino acid residues have been conservatively or non-conservatively substituted. Examples of conservative substitutions include the substitution of a non-polar (hydrophobic) residue such as isoleucine, valine, leucine or methionine for another. Likewise, the present invention contemplates the substitution of one polar (hydrophilic) residue such as between arginine and lysine, between glutamine and asparagine, and between glycine and serine. Additionally, the substitution of a basic residue such as lysine, arginine or histidine for another or the substitution of one acidic residue such as aspartic acid or glutamic acid for another is also contemplated. Examples of non-conservative substitutions include the substitution of a non-polar (hydrophobic) residue such as isoleucine, valine, leucine, alanine, methionine for a polar (hydrophilic) residues such as cysteine, glutamine, glutamic acid, lysine and/or a polar residue for a non-polar residue.

The phrase "conservative substitution" also includes the use of chemically derivatized residues in place of a non-derivatized residues as long as the peptide retains the requisite IL-17 blocking properties as conventionally measured by the MLR assay (Theodore et al., J. Immunol. 157:1958-1964 (1996)). Analogs also include the presence of additional amino acids or the deletion of one or more amino acids which do not affect IL-17-mediated biological activity. For example, analogs of the subject peptides can contain an N- or C-terminal cysteine, by which, if desired, the peptide may be covalently attached to a carrier protein, e.g., albumin. Such attachment can decrease clearing of the peptide from the blood and also decrease the rate of proteolysis of the peptides. In addition, for purposes of the present invention, peptides containing D-amino acids in place of L-amino acids are also included in the term "conservative substitution." The presence of such D-isomers can help minimize proteolytic activity and clearing of the peptide.

Ordinarily, the conservative substitution variants, analogs, and derivatives of the peptides, will have an amino acid sequence identity to the disclosed sequences of at least about 55%, at least about 65%, at least about 75%, at least about 80%, at least about 85%, at least about 90%, at least about 95%, or at least about 96% to 99%. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Preparation of Decoy Peptides

The decoy peptides of the present invention, and homologs, analogs and fragments thereof, may be synthesized by a number of known techniques. For example, the peptides may be prepared using the solid-phase synthetic technique initially described by Merrifield in J. Am. Chem. Soc. 85:2149 2154 (1963). In general, the method comprises the sequential addition of one or more amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine. Other peptide synthesis techniques may be found in M. Bodanszky, et al. Peptide Synthesis, John Wiley & Sons, 2d Ed., (1976) and other references readily available to those skilled in the art. A summary of polypeptide synthesis techniques can be found in J. Stuart and J. D. Young, Solid Phase Peptide Synthesis, Pierce Chemical Company, Rockford, Ill., (1984). Peptides may also be synthesized by solution methods as described in The Proteins, Vol. II. 3d Ed., Neurath, H. et al., Eds., p. 105 237, Academic Press, New York, N.Y. (1976). Appropriate protective groups for use in different peptide syntheses are described in the above-mentioned texts as well as in J. F. W. McOmie, Protective Groups in Organic Chemistry, Plenum Press, New York, N.Y. (1973). The peptides of the present invention can also be prepared by chemical or enzymatic cleavage from larger portions of the IL-17R or Act1 molecule or from the entire the IL-17R or Act1 molecule.

A preferred method of solid phase peptide synthesis entails attaching the protected or derivatized amino acid to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino carboxyl group is then removed from this newly added amino acid residue, and the next amino acid (suitably protected) is then added, and so forth. After all the desired amino acids have been linked in the proper sequence, any remaining terminal and side group protecting groups including the solid support are removed sequentially or concurrently to yield the final peptide. The lyophilized oligopeptides are resuspended in double distilled $H_2O$ at 2 mg/ml as stock solutions and subsequently diluted in M199-HPS for experiments.

Additionally, the peptides of the present invention may also be prepared by recombinant DNA techniques (see e.g. Current Protocols in Molecular Cloning Ausubel et al., 1995, John Wiley & Sons, New York); Sambrook et al., 1989, Molecular Cloning: A Laboratory Manual, Second Edition, Cold Spring Harbor Laboratory Press, New York; Coligan et al. Current Protocols in Immunology, John Wiley & Sons Inc., New York, N.Y. (1994)). The skilled artisan understands that any of a wide variety of expression systems can be used to provide the recombinant peptides of the present invention. The precise host cell used is not critical to the invention. The decoy peptides can be produced in a prokaryotic host (e.g. *E. coli*), or in a eukaryotic host (e.g., *S. cerevisiae* or mammalian cells, e.g. COS1, CHO, NIH3T3, and JEG3 cells, or in the cells of an arthropod, e.g. *S. frugiperda*). Such cells are available from e.g. the American Type Culture Collection, Manassas, Va. The method of transfection and the choice of expression vehicle will depend on the host system selected. Transformation and transfection methods are described, e.g. in Sambrook et al. supra; expression vehicles can be chosen from those provided e.g. in Cloning Vectors: A Laboratory Manual P. H. Powels et al. (1985), Supp. 1987.

For most of the amino acids used to build proteins, more than one coding nucleotide triplet (codon) can code for a particular amino acid residue. This property of the genetic code is known as redundancy. Therefore, a number of different nucleotide sequences can code for a particular subject decoy peptide. The present invention also contemplates a deoxyribonucleic acid (DNA) molecule or segment that defines a gene coding for, i.e., capable of expressing, a subject peptide or a subject chimeric peptide from which a peptide of the present invention may be enzymatically or chemically cleaved.

DNA molecules that encode peptides of the present invention can be synthesized by chemical techniques, for example, the phosphotriester method of Matteuccie, et al., J. Am. Chem. Soc. 103:3185 (1981). Using a chemical DNA synthesis technique, desired modifications in the peptide sequence can be made by making substitutions for bases which code for the native amino acid sequence. Ribonucleic acid equivalents of the above described DNA molecules may also be used.

As used herein, the term "polynucleotide" refers to oligonucleotides, nucleotides, or to a fragment of any of these, to DNA or RNA (e.g., mRNA, rRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, siRNAs, microRNAs, and ribonucleoproteins. The term also encompasses nucleic acids, i.e., oligonucleotides, containing known analogues of natural nucleotides, as well as nucleic acid-like structures with synthetic backbones.

A nucleic acid molecule comprising a vector capable of replication and expression of a DNA molecule defining coding sequence for a subject polypeptide or subject chimeric polypeptide is also contemplated.

Protein Transduction Domains

The present invention includes administering a therapeutically effective amount of a cell-permeable decoy peptide to a subject. Cell permeable decoy peptides are peptides that are able to overcome the cell membrane barrier and enter a cell to interfere with SEFIR-SEFIR interactions. A preferred method of enhancing cell permeation by decoy peptides is the use of a protein transduction domain (PTD). PTDs can be conjugated to a decoy peptide to facilitate cell-permeation by the decoy peptide. PTDs are heterogeneous in size and lack sequence homology, although most share a positive charge and are amphipathic. The PTDs of the present invention are those that facilitate intracellular transport. In certain embodiments, PTDs can be antimicrobial peptides such as protegrin 1, Bactenecin 7, Buforin, and Maginin; a host of arginine-rich RNA- and DNA-binding peptides (e.g., HIV-1 transactivating protein (TAT) and Drosophila homeodomain transcription factor Antennapedia (a.k.a. Penetratin); chimeric PTDs such as Transportan; lysine- and arginine-rich peptides derived from phage-display libraries; polyarginine; and most recently, β-homolysine oligomers (See, Fisher et al., Bioconjugate Chemistry 12: 825-841 (2001); Lindsay, Current Opinions in Pharmacology 2: 587-594 (2002); Tung et al., Advanced Drug Delivery Reviews 55: 281-294 (2003); Leifert et al., Molecular Therapy 8: 13-19 (2003); Bogoyevitch et al., DNA and Cell Biology 21: 879-894 (2002); Garcia-Echeverria et al., Bioorganic & Medicinal Chemistry Letters 13: 247-251 (2003), incorporated herein by reference in their entireties). In certain embodiments, the PTDs are addition, reverso-, retro-inverso, and enantio-forms of many of the PTDs described herein.

Examples of specific PTD conjugates suitable for use with a decoy peptide include GRKKRRQRRRPPQ (SEQ. ID. NO. 10); DRQIKIWFQNRRMKWKK (SEQ. ID. NO. 11); RRMKWKK (SEQ. ID. NO. 12); RGGRLSYSRRRFST-STGR (SEQ. ID. NO. 13); RRLSYSRRRF (SEQ. ID. NO. 14); RGGRLAYLRRRWAVLGR (SEQ. ID. NO. 15); and RRRRRRRR (SEQ. ID. NO. 16). The PTD conjugates can be directly linked to the decoy peptide, or a number of intervening linking peptides can be included between the decoy peptide and the PTD. For example, from 1-10 intervening linking peptides can be included. An example of a decoy peptide that is directly conjugated to a PTD is provided by the amino acid sequence DRQIKIWFQNRRM-KWKKLDEDEHGLHTKY (SEQ ID NO: 17).

In some embodiments, the decoy peptide can be conjugated to a protein transduction domain that is derived from Antennapedia. The PTD can alternatively include all or part of the Drosophila Antennapedia (Antp) homeodomain (HD) protein. For example, the PTD may comprise the third helix of Antp-HD, which has cell penetration properties. The region responsible for translocation in Antp-HD has been localized to amino acids 43-58 (i.e., the third helix), a 16 amino acid-long peptide rich in basic amino acids. The third helix has the amino acid sequence DRQIKIWFQNRRMK-WKK (SEQ ID NO: 11). This polypeptide has been used to direct biologically active substances to the cytoplasm and nucleus of cells in culture. Accordingly, the PTD conjugated to a decoy peptide the present invention may comprise an Antp-HD polypeptide, an Antp-HD homolog, an Antp-HD variant, and/or an Antp-HD fragment, such as a fragment containing the third helix of Antp-HD, for example.

Protein transduction domains can be linked to the other amino acids of the decoy peptide by chemical cross-linking or by other techniques known to those skilled in the art, such as recombinant techniques. For example, a PTD can be fused to an amino acid sequence substantially homologous to at least a portion of the αC helix region of the SEFIR domain of Act1 or an amino acid sequence substantially homologous to at least a portion of the αC helix region of the SEFIR domain of IL-17R by expression in a suitable eukaryotic or prokaryotic host cell. The fused protein can be expressed by introducing a cDNA sequence encoding the fused protein together with an N-terminal leader sequence (e.g., a 6-histidine tag) (SEQ ID NO: 18) to enable purification of the expressed cell-permeable decoy peptide. Alternately, the amino acid sequence based on the SEFIR domain can include a linker sequence that operably couples the PTD with the amino acids of the SEFIR domain.

While any of the PTDs (including domains and/or sequences and/or fragments thereof exhibiting membrane translocation activity) provided above may be used for the purpose of generating a cell-permeable polypeptide, it should be appreciated that other variations are also possible. For example, variations such as mutations (e.g., point mutations, deletions, insertions, etc.) of any of the sequences disclosed herein may be employed, provided that some membrane translocation activity is retained. Furthermore, it will be appreciated that homologues of PTDs from any other organism, including those of synthetic origin, may also be used.

IL-17 Mediated Disease

In the context of the present invention, the term "IL-17-mediated" refers to an activity of interleukin-17 (IL-17) or a signal transduction pathway involving or mediated by IL-17. IL-17 includes all IL-17 subtypes, such as IL-17A, IL-17B, IL-17C, IL-17D, IL-17E, and IL-17F. All members of the IL-17 family have a similar protein structure, with four highly conserved cysteine residues critical to their 3-dimensional shape, but have no significant sequence similarity to any other known cytokines. Thus, an IL-17-mediated disease is a disease in which IL-17 activity can be modulated for treatment of the disease. More particularly, the present invention encompasses compositions and methods that modulate an IL-17 activity and/or IL-17 signal transduction pathway to provide a therapeutic benefit or therapeutic activity for treatment of an inflammatory or autoimmune disease.

As used herein, the term "activity" with reference to IL-17 activity refers to a cellular, biological, and/or therapeutic activity or function of IL-17. Examples of such activities can include, but are not limited to, signal transduction, interacting or associating with an IL-17 receptor or other binding partner (e.g., Act1) or cellular component, and modulating asthma or an inflammatory response or process. As further described herein, Act1 is an essential component in signaling by IL-17, and effectuates signaling by binding to IL-17R complexes in a SEFIR-dependent manner. IL-17 activity also refers to the production of many other cytokines (such as IL-6, G-CSF, GM-CSF, IL-1β, TGF-β, TNF-α), chemokines (including IL-8, GRO-α, and MCP-1), and prostaglandins (e.g., PGE2) from many cell types (fibroblasts, endothelial cells, epithelial cells, keratinocytes, and macrophages)

that can be induced by IL-17. The release of cytokines causes many functions, such as airway remodeling, a characteristic of IL-17 responses.

The IL-17-mediated disease can include a disease where an IL-17 activity or an IL-17-dependent signal transduction pathway can be modulated for treatment of the disease. Examples of IL-17-mediated diseases include, but are not limited to inflammatory diseases (e.g., asthma, inflammatory bowel disease, multiple sclerosis, experimental autoimmune encephalomyelitis, and allergen-induced pulmonary inflammation) and autoimmune diseases (e.g., systemic lupus erythematosus, rheumatoid arthritis, allograft rejection, drug-induced lupus and psoriasis). It should be noted that there is significant overlap between inflammatory disease and autoimmune disease. For example, inflammatory disease includes an abnormal activation of the immune system, and autoimmune disease often involves undesirable levels of inflammation. IL-17 also involved in allergic responses (e.g., dust mite-induced allergic asthma), and immune responses to an infectious agent (e.g., a bacterium or virus) and antitumor immunity.

As used herein, the term "inflammatory disease" refers to a disease characterized by activation of the immune system to abnormal levels that lead to the disease. Accordingly, inflammatory diseases that do not involve abnormal activation of the immune system, such as atherosclerosis or ischemic heart disease, are not included in the definition used herein. An inflammatory disease can include a state in which there is a response to tissue damage, cell injury, an antigen, an infectious disease, and/or some unknown cause. Symptoms of inflammation may include, but are not limited to, cell infiltration and tissue swelling.

An inflammatory disease of particular interest is asthma. Endogenous IL-25 has been shown to be critical in allergen-induced pulmonary airway hyperreactivity and inflammation in a mouse model of asthma. Asthma is a common chronic inflammatory disease of the airways characterized by variable and recurring symptoms, reversible airflow obstruction, and bronchospasm. Diagnosis of asthma is not precise, and physicians are recommended to use spirometry whenever possible to guide the diagnosis and management of asthma.

As used herein, the term "autoimmune disease" refers to a disease that arises from an inappropriate immune response of the body against substances and tissues that are normally present in the body. In other words, the immune system mistakes some part of the body as a pathogen and attacks its own cells. Autoimmune disease may be restricted to certain organs (e.g. in autoimmune thyroiditis) or involve a particular tissue in different places within the body. For a disease to be regarded as an autoimmune disease, it is generally necessary to provide direct evidence by obtaining a sample of the pathogenic antibody or pathogenic T cells, or as a result of indirect evidence based on reproduction of the autoimmune disease in experimental animals.

Suitable subjects benefiting from the methods of the present invention include male and female mammalian subjects, including humans, non-human primates, and non-primate mammals. Other suitable mammalian subjects include domesticated farm animals (e.g., cow, horse, pig) or pets (e.g., dog, cat).

As used herein, the terms "treatment," "treating," or "treat" refer to any treatment of an IL-17-mediated disease in a subject including, but not limited to, inhibiting disease development, arresting development of clinical symptoms associated with the disease, and/or relieving the symptoms associated with the disease. Prophylactic treatment or prevention refers to preventing the disease from developing. However, the terms "treating" and "ameliorating" do not necessarily meant to indicate a reversal or cessation of the disease process underlying the asthma or inflammation afflicting the subject being treated. Such terms indicate that the deleterious signs and/or symptoms associated with the condition being treated are lessened or reduced, or the rate of progression is reduced, compared to that which would occur in the absence of treatment. A change in a disease sign or symptom can be assessed at the level of the subject (e.g., the function or condition of the subject is assessed), or at a tissue or cellular level (e.g., the production of markers of asthma or inflammation is lessened or reduced).

Administration of Decoy Peptides

The peptides of the present invention can be administered acutely (i.e., during the onset or shortly after events leading to inflammation or autoimmune disease), or can be administered prophylactically (e.g., before scheduled surgery, or before the appearance of signs or symptoms), or administered during the course of inflammation or autoimmune disease to reduce or ameliorate the progression of symptoms that would otherwise occur. The timing and interval of administration is varied according to the subject's symptoms, and can be administered at an interval of several hours to several days, over a time course of hours, days, weeks or longer, as would be determined by one skilled in the art.

The compositions containing the decoy peptides are generally administered intravenously to inhibit, suppress, or cause the cessation of at least one IL-17-mediated biological activity. When administered intravenously, the peptide compositions may be combined with other ingredients, such as carriers and/or adjuvants. The peptides may also be covalently attached to a protein carrier, such as albumin, so as to minimize clearing of the peptides. There are no limitations on the nature of the other ingredients, except that such ingredients must be pharmaceutically acceptable, efficacious for their intended administration and cannot degrade the activity of the active ingredients of the compositions. Examples of other anti-inflammatory ingredients contemplated by the present invention include, but are not limited to anti-IL-17 antibodies, anti-TNFα antibodies, NSAIDS, steroids, or cyclosporin-A. When employed together with decoy peptides, these agents may be employed in lesser dosages than when used alone.

The pharmaceutical forms suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants or vegetable oils. Sterilization can be accomplished by any art-recognized technique, including but not limited to, filtration or addition of antibacterial or antifungal agents, for example, paraben, chlorobutano, phenol, sorbic acid or thimerosal. Further, isotonic agents such as sugars or sodium chloride may be incorporated in the subject compositions.

Production of sterile injectable solutions containing the subject peptides is accomplished by incorporated these compounds in the required amount in the appropriate solvent with various ingredients enumerated above, as required, followed by sterilization, preferably filter sterilization. To obtain a sterile powder, the above solutions are vacuum-dried or freeze-dried as necessary. The decoy peptides are preferably isolated, as defined herein, before inclusion in a pharmaceutical form such as an injectable solution.

When the peptides of the invention are administered orally, the pharmaceutical compositions thereof containing an effective dose of the peptide can also contain an inert diluent, as assimilable edible carrier and the like, be in hard or soft shell gelatin capsules, be compressed into tablets, or may be in an elixir, suspension, syrup or the like. The subject peptides are thus compounded for convenient and effective administration in pharmaceutically effective amounts with a suitable pharmaceutically acceptable carrier in a therapeutically effective amount.

The expressions "effective amount" or "therapeutically effective amount," as used herein, refers to a sufficient amount of agent to interfere with the interaction between Act1 and IL-17 and to exhibit a therapeutic effect. The exact amount required will vary from subject to subject, depending on the species, age, and general condition of the subject, the particular therapeutic agent, its mode and/or route of administration, and the like. It will be understood, however, that the total daily usage of the compounds and compositions of the present invention can be decided by an attending physician within the scope of sound medical judgment. The specific therapeutically effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific composition employed; the duration of the treatment; drugs used in combination or coincidental with the specific composition employed; and like factors well known in the medical arts.

The peptides can be administered in a manner compatible with the dosage formulation and in such amount as well be therapeutically effective. Systemic dosages depend on the age, weight and conditions of the patient and on the administration route. For example, a suitable dose for the administration to adult humans ranges from about 0.001 to about 20.0 mg per kilogram of body weight. The peptides should preferably be administered in an amount of at least about 50 mg per dose, more preferably in an amount up to about 500 mg to about 1 gram per dose. Since the peptide compositions of this invention will eventually be cleared from the bloodstream, re-administration of the compositions is indicated and preferred.

As used herein, a pharmaceutically acceptable carrier includes any and all solvents, dispersion media, coatings, antibacterial and antifungal agents, isotonic agents the like. The use of such media and agents are well-known in the art. The pharmaceutically acceptable carriers used in conjunction with the peptides of the present invention vary according to the mode of administration. For example, the compositions may be formulated in any suitable carrier for oral liquid formulation such as suspensions, elixirs and solutions. Compositions for liquid oral dosage include any of the usual pharmaceutical media such as, for example, water, oils, alcohols, flavoring agents, preservatives, coloring agents and the like. In the case of oral solid preparations (capsules and tablets) carriers such as starches, sugars, diluents, granulating agents, lubricants, binders, disintegrating agents and the like may be used. In addition, carriers such as liposomes and microemulsions may be used.

Antibodies Against IL-17R or Act1

The SEFIR domain of IL-17R or Act1 (or homologs, analogs or fragments thereof) can also be used as a substrate to raise antibodies. In particular, the αC helix portion of the SEFIR domain of either IL-17R or Act1 can be used can be used as a substrate to generate antibodies have an affinity for this region. Because of their affinity for at least a portion of the SEFIR domain, these antibodies can be used in a manner similar to peptide decoys to interfere with the SEFIR-SEFIR interaction involved in the association of Act1 with IL-17R. Accordingly, antibodies specific for the SEFIR domain of either IL-17R or Act1 can be used to treat IL-17-mediated diseases.

As used herein, the term "antibody" refers to whole antibodies, e.g., of any isotype (IgG, IgA, IgM, IgE, etc.) and includes fragments thereof, which are also specifically reactive with a target polypeptide. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain polypeptide, such as single-chain antibodies (SAb). Non-limiting examples of such proteolytic and/or recombinant fragments include Fab, F(ab')$_2$, Fab', Fv, and SAb containing a V[L] and/or V[H] domain joined by a peptide linker. The SAb's may be covalently or non-covalently linked to form antibodies having two or more binding sites. The term "antibody" also includes polyclonal, monoclonal, nanobodies, or other purified preparations of antibodies, recombinant antibodies, monovalent antibodies, and multivalent antibodies. Antibodies may be humanized and may further include engineered complexes that comprise antibody-derived binding sites, such as diabodies and triabodies.

To facilitate generation of the antibodies, the substrate peptides can be coupled to a carrier protein such as KLH as described in Ausubel et al. (1989) Current Protocols in Molecular Biology, John Wiley & Sons, New York. The KLH-antagonist peptide is mixed with Freund's adjuvant and injected into guinea pigs, rats, donkeys and the like or preferably into rabbits. A single-chain antibody (SAb) is created by fusing together the variable domains of the heavy and light chains using a short peptide linker, thereby reconstituting an antigen binding site on a single molecule. Such single-chain antibody variable fragments (Fvs) can be fused to all or a portion of the constant domains of the heavy chain of an immunoglobulin molecule, if necessary. Single chain antibodies and methods for their production are known in the art. See, e.g., Bedzyk et al. (1990) J. Biol. Chem., 265:18615; Chaudhary et al. (1990) Proc. Natl. Acad. Sci., 87:9491; U.S. Pat. No. 4,946,778 to Ladner et al.; and U.S. Pat. No. 5,359,046 to Capon et al. Antibodies may be purified, for example, by peptide antigen affinity chromatography.

Monoclonal antibodies can be prepared using peptides obtained from at least a portion of the SEFIR domain of IL-17R or Act1 using standard hybridoma technology (see e.g. Kohler et al., (1975) Nature 256:495; Hammerling et al., (1981) In Monoclonal Antibodies and T Cell Hybridomas, Elsevier, New York). A preferred region of the SEFIR domain is the αC helix region. For example, monoclonal antibodies to IL-17R or Act1 (and homologs, analogs or fragments thereof) can be raised in Balb/C or other similar strains of mice by immunization with purified or partially purified preparations of the SEFIR domain of IL-17R or Act1. The spleens of the mice can be removed, and their lymphocytes fused to a mouse myeloma cell line. After screening of hybrids by known techniques, a stable hybrid will be isolated that produces antibodies against the IL-17R or Act1 SEFIR domain peptides. The activity of the antibodies can be demonstrated by their ability to prevent the binding of radiolabelled IL-17R to Act1 (or vice versa). The monoclonal antibody can then be examined for its ability to inhibit the biological activity of IL-17, e.g. on airway remodeling. Once produced, monoclonal antibodies are tested for specific IL-17 recognition by Western blot or immunoprecipitation analysis (using methods described in Ausubel et al., supra).

Monoclonal antibodies of the present invention can be humanized to reduce the immunogenicity for use in humans. One approach is to make mouse-human chimeric antibodies having the original variable region of the murine mAb, joined to constant regions of a human immunoglobulin. Chimeric antibodies and methods for their production are known in the art. See, e.g., Sun et al., Proc. Natl. Acad. Sci. USA 84:214 218 (1987); Better et al., Science 240:1041 1043 (1988). Generally, DNA segments encoding the H and L chain antigen-binding regions of the murine mAb can be cloned from the mAb-producing hybridoma cells, which can then be joined to DNA segments encoding $C_H$ and $C_L$ regions of a human immunoglobulin, respectively, to produce murine-human chimeric immunoglobulin-encoding genes.

Discussion of the Mechanism of SEFIR-SEFIR Interactions

The inventors have identified an interaction interface (the CC' loop) in the SEFIR domains of several interacting SEFIR family members, including IL-17RA, IL-17RB, IL-17RC, and Act1, as described in the Examples herein. Deletion of the CC' loop from either Act1 or IL-17RA disrupted the interaction between IL-17R and Act1. The isolated CC' loop of Act1 bound directly to IL-17RA, and point mutations in the CC' loop region abolished IL-17- and IL-25-mediated signaling and target gene expression. Furthermore, a cell-permeable decoy peptide based on the CC' loop interfered with IL-17- and IL-25-mediated signaling in cell culture and attenuated IL-17- and IL-25-induced pulmonary inflammation in mice. Subsequent work, also described herein, indicates that the secondary structure in which the sequences of interest are found is an αC helix, rather than a CC' loop. Together, the findings indicate that the αC helix motif of the SEFIR domain of Act1 is a promising therapeutic target to attenuate IL-17-mediated diseases.

The inventors' studies provide blocking peptides or peptidomimetic compounds for treating IL-17-mediated diseases. That IL-17 and IL-17E (IL-25) signaling participate in allergic airway inflammation makes the Act1 SEFIR domain αC helix decoy peptide a promising template for the development of future therapeutics for asthmatic patients. IL-17 has a more prominent role than does IL-25 in the pathogenic processes of human and animal autoimmune diseases, such as rheumatoid arthritis, inflammatory bowel disease, multiple sclerosis, and experimental autoimmune encephalomyelitis. The Act1 SEFIR domain αC helix decoy peptide may also be useful against various IL-17-dependent autoimmune disorders.

Although the αC helix is required for the interaction of Act1 with receptors (through heterotypic SEFIR-SEFIR domain interactions), other surface-exposed regions in the SEFIR domain may be important for receptor-receptor and Act1-Act1 homotypic SEFIR domain interactions. Previous studies have demonstrated the occurrence of IL-17RA-IL-17RB (IL-25R) and IL-17RA-IL-17RC (IL-17R) interactions. Rickel et al., J Immunol 181:4299-4310 (2008), Toy et al., J Immunol 177:36-39 (2006). The inventors have applied both mutagenesis and decoy peptide approaches to study the homotypic interactions of SEFIR domains and their impact on IL-17 versus IL-25 signaling, and to identify additional, receptor-specific, SEFIR decoy peptides.

The inventors have also obtained the structure of the SEFIR domain from IL-17RB at 1.8 Å resolution, providing the first atomic view at the unique signaling module that is signature for IL-17 intracellular signaling. This work revealed key structural elements involved in IL-17RB mediated signaling. The structural and functional analysis of IL-17RB-SEFIR identified the helix αC as a critical structural motif for heterotypic SEFIR-SEFIR interactions between Act1 and IL-17RB. Specifically, the inventors have shown single mutations at residue L419 or L422 that are located on the surface of helix αC of IL-17RB-SEFIR abolished the interaction with Act1 and gene expression stimulated by IL-17E (IL-25).

Previously the inventors identified a unique region (residues 467-478) in Act1-SEFIR critical for heterotypic association with IL-17RA-SEFIR. In the absence of any structure information on SEFIR, the earlier homology modeling predicted the secondary structure of this region as a loop, termed CC' loop, based on a distantly related TIR domain as the template. Deletion or mutations in this region of Act1-SEFIR disrupted its hetero-dimerization with IL-17RA and suppressed IL-17A- and IL-17E (IL-25)-dependent signaling. Liu et al., Sci Signal 4: ra72 (2011). In addition, a cell permeable decoy peptide derived from the A.A. sequence of this CC' loop disrupts the Act1-IL-17RA interaction and inhibits IL-17A- and IL-17E (IL-25)-induced pulmonary inflammation The high-resolution crystal structure of IL-17RB-SEFIR provides a better structural template for the new attempt of the homology modeling of Act1-SEFIR, another member of the same SEFIR family. The functionally essential residues (L474, H475, K477 and Y478), located on the previously defined CC' loop in Act1-SEFIR domain, are now all mapped on the N-terminal section of the helix αC. The structure based sequence alignment obtained shows the helix αC as a conserved structural feature for SEFIR domains among IL-17RA, RB, RC and Act1. Collectively, the data indicate that the helix αC is a conserved structural motif that is important for heterotypic SEFIR-SEFIR interactions. Docking the modeled Act1-SEFIR structure with IL-17RB-SEFIR crystal structure showed their heterotypic interactions are predominantly clustered at helix αC and the tip of helix αB, with helix αB' largely exposed on the surface and available for potential homotypic interactions. The data imply a dual ligand-binding mode for SEFIR domain with different structural motifs engaging in either homo- or hetero-SEFIR-SEFIR associations.

The following examples are included for purposes of illustration and are not intended to limit the scope of the invention.

EXAMPLES

Example 1

The SEFIR3 Region is Critical for Interactions Between the Act1 SEFIR Domain and IL-17RA Act1 acts as an intermediate signaling component that is recruited to IL-17RA through heterodimeric interactions between their SEFIR domains. The inventors wanted to determine whether disruption of this SEFIR-SEFIR domain interaction was a feasible strategy to block IL-17 and IL-25 signaling. First, the SEFIR domains that were critical for this interaction were mapped by constructing deletion mutants of the Act1 SEFIR domain (FIG. 1A). These mutants, designated SEFIR1 to SEFIR5, were generated as a result of deletions of five exons that encode regions of the SEFIR domain, corresponding to amino acid residues 391 to 420, 421 to 443, 444 to 482, 483 to 507, and 508 to 537, respectively. HeLa cells were cotransfected with plasmids encoding FLAG-tagged wild-type Act1 or its SEFIR deletion mutants (D-SEFIR1 to D-SEFIR5) together with plasmid encoding the V5-tagged IL-17RA. Whereas D-SEFIR1, D-SEFIR2, D-SEFIR4, and D-SEFIR5 retained similar interactions with IL-17RA as occurred with wild-type Act1, the D-SEFIR3 deletion mutant of Act1 did not interact with the receptor (FIG. 1B). Furthermore, the D-SEFIR3 mutant Act1 was unable to restore IL-17-induced expression of Cxcl1 and IL-25-induced expression of␣l13 in transfected Act1$^{-/-}$ mouse embryonic fibroblasts (MEFs) (FIG. 1C). These data demonstrate that SEFIR3 is a critical region for the interaction between Act1 and IL-17RA as well as for IL-17- and IL-25-dependent signaling.

Example 2

A CC' Loop Peptide Derived from SEFIR3 Binds Directly to IL-17RA

Based on sequence homology, SEFIR domains are thought to resemble TIR domains in their secondary and tertiary structures. Novatchkova et al., Trends Biochem Sci 28:226-229 (2003). Computational modeling of the SEFIR domain of Act1 was therefore carried out with I-Tasser software. Roy et al., Nat Protoc 5:725-738 (2010). Although initial homology templates were not explicitly specified, most of the templates selected by I-Tasser were TIR domains from TLR2, TLR4, TLR10, and the TLR adaptor protein MyD88 (myeloid differentiation primary response gene 88). A homology model of the Act1 SEFIR domain showed a central five-stranded β-sheet structure surrounded by five roughly parallel helices (FIG. 2), which closely resembled the canonical TIR domain fold; however, an additional helix ($C_{ins}$) was inserted between the third strand (C) and third helix (C') of the Act1 SEFIR domain. Similar to TIR domains, the loop between the second strand and the second helix (the BB' loop) of the Act1 SEFIR domain was prominent. Whereas previous studies have shown that the BB' loop is required for the TIR-TIR domain interaction, the inventors found that deletion of a segment containing the BB' loop (as occurred in the SEFIR2 mutant) (FIG. 1A and FIG. 2) did not affect the interaction between Act1 and IL-17RA (FIG. 1B). The D-SEFIR3 Act1 mutant, from which the Cins helix and the CC' loop (which connects $C_{ins}$ to the C' helix) were deleted, did not interact with IL-17RA (FIG. 1B), suggesting that SEFIR domains interact with each other in a manner different from that of TIR domains.

The $C_{ins}$ helix and the CC' loop are distinct putative surface-exposed sequences in the SEFIR3 segment of Act1. To determine whether the $C_{ins}$ helix and the CC' loop interacted with IL-17RA, surface plasmon resonance (SPR) was used to test peptides derived from $C_{ins}$ (SPKYKQDVEGAESQ) (SEQ ID NO: 19) and the CC' loop (LDEDEHGLHTKY) (SEQ ID NO: 5) for their ability to bind to the IL-17RA SEFIR domain. As expected, the recombinant Act1 SEFIR domain bound to the sensor-immobilized SEFIR of IL-17RA. The inventors found that the CC' loop peptide, but not the $C_{ins}$ peptide, bound to the IL-17RA SEFIR. Furthermore, a peptide derived from the BB' loop of the Act1 SEFIR domain (EDRIRGID) (SEQ ID NO: 20) did not bind to the IL-17RA SEFIR domain. This result was consistent with earlier data that showed that deletion of the BB' loop did not affect the interaction between Act1 and IL-17RA (FIG. 1B, D-SEFIR2 mutant). The SPR data suggested that the CC' loop might mediate the interaction between the Act1 SEFIR domain and IL-17RA.

Example 3

Figure 3:
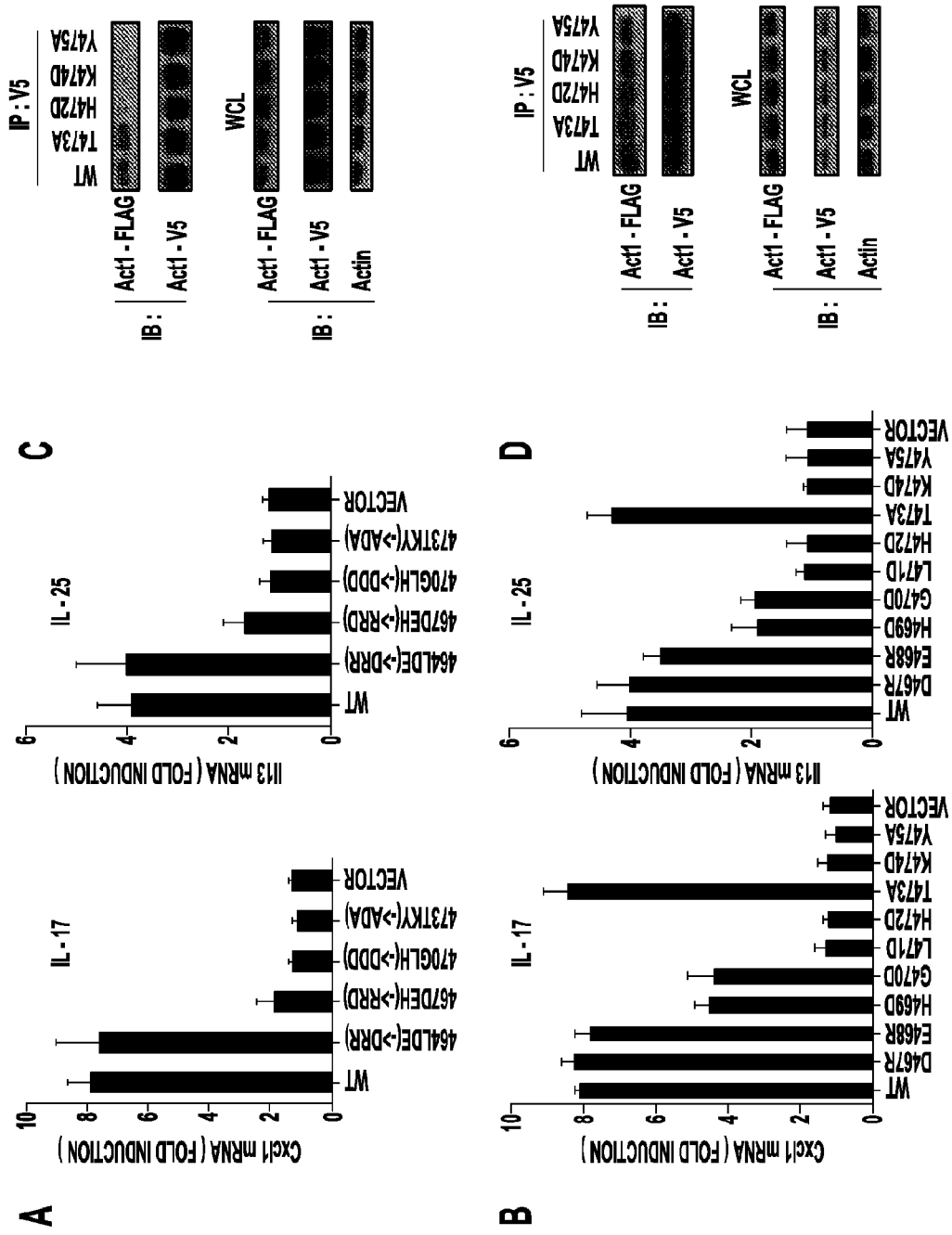
FIG. 3 shows that mutations in the CC' loop region of the Act1 SEFIR domain disrupt its interaction with IL-17RA and inhibit IL-17 and IL-25 signaling.

Mutations in the CC' Loop Region of the Act1 SEFIR Domain Disrupt its Interaction with IL-17RA and Suppress IL-17- and IL-25-Depedent Signaling To identify the residues within the CC' loop region that affected the interaction between Act1 and the IL-17RA, point mutations were introduced within the CC' loop. First, four mutants of Act1 that contained three amino acid (3-AA) point mutants were generated by replacing each residue in the group of three with a residue of a different charge (FIG. 3A). Three of these mutant proteins (with point mutations located between residues 467 and 475) could not restore IL-17- and IL-25-mediated gene expression in Act1−/− MEFs (FIG. 3A), which suggested that these CC' loop residues were critical for the interaction between Act1 and the IL-17RA. Next nine single-residue point mutants were used to map specific residues that were critical for IL-17RA signaling in more detail. Four point mutants of Act1 (G470D, L471D, K474D, and Y475A) were unable to restore IL-17- or IL-25-mediated gene expression in Act1$^{-/-}$ MEFs (FIG. 3B). Of these mutants, three (L471D, K474D, and Y475A) exhibited almost no interaction with IL-17 RA (FIG. 3C). Because Act1 can form homodimers or homomeric multimers through its SEFIR domain, the inventors tested whether residues important for the interaction between Act1 and IL-17RA were also important for Act1-Act1 associations. They found that the L471 D, K474D, and Y475A mutants retained the ability to form Act1-Act1 interactions (FIG. 3D), suggesting that Act1 may use distinct interfaces for IL-17 RA interaction and for self-association. These results indicated that the CC' loop region of the Act1 SEFIR domain was critical for Act1-IL-17RA interactions and for IL-17- and IL-25-dependent signaling.

Example 4

Figure 4:
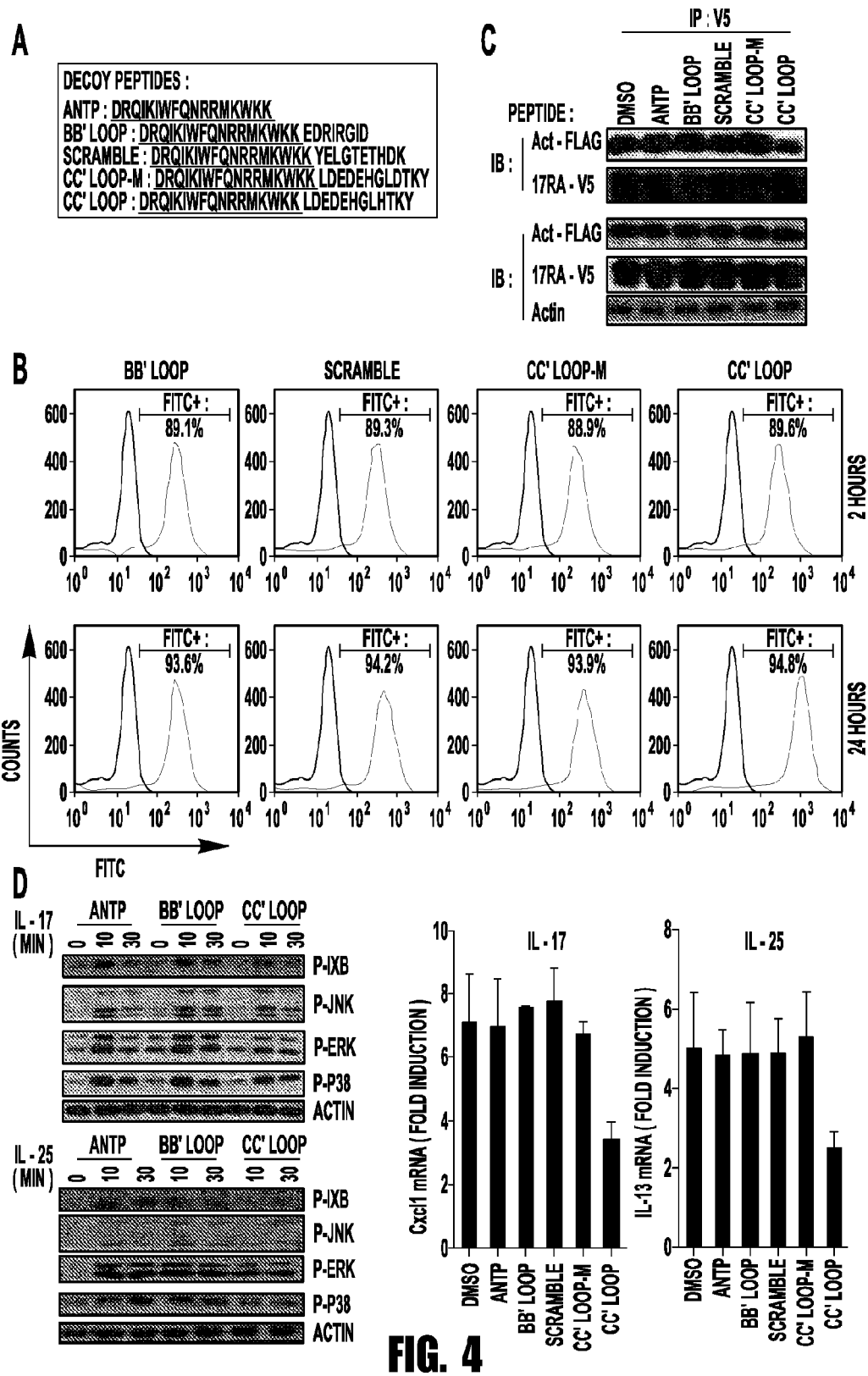
FIG. 4 provides data showing that a cell-permeable CC' loop decoy peptide disrupts the interaction between Act1 and IL-17RA and inhibits IL-17R and IL-25R signaling.

A Cell-Permeable CC' Loop Decoy Peptide Disrupts the Act1-IL-17RA Interaction and Inhibits IL-17-Dependent and IL-25-Dependent Signaling Decoy peptides are based on surface-exposed regions of the primary sequence of a protein to mimic a putative interaction interface. A well-folded decoy peptide often has the ability to bind to and occupy the docking site of the interacting partner of the original protein, and this binding then prevents the protein-protein interaction and inhibits downstream signaling. Cell-permeable TIR BB' loop decoy peptides have been successfully used to inhibit TLR signaling. Toshchakov et al., Expert Opin Biol Ther 7:1035-1050 (2007). Cell-permeable decoy peptides were designed that contained the BB' loop or CC' loop sequences of the Act1 SEFIR domain fused to the C-terminus of the translocating segment of the antennapedia homeodomain (Antp: DRQIKIWFQNRRMKWKK) (SEQ ID NO: 11) (FIG. 4A). Antp sequence was identified in the homeodomain of the Drosophila transcription factor, antennapedia, and is well known for its ability to penetrate cell membrane and carry cargo peptides into cells. These decoy peptides were also tagged at their C-termini with fluorescein isothiocyanate (FITC) to enable their cell-penetrating efficiency to be evaluated by flow cytometric sanalysis. It was found that all of the peptides had similar cell permeabilities, and that incubation of the cells with the peptides for 24 hours enabled maximal cell-penetrating efficiency without causing any noticeable adverse effects (FIG. 4B). The decoy peptides were then compared for their ability to inhibit the interaction between Act1 and the IL-17RA. The Act1 SEFIR domain CC' loop peptide more efficiently inhibited the Act1-IL-17RA interaction than did the Act1 SEFIR domain BB' loop peptide, the scrambled peptide, and the mutant (CC' loop-M, H472→D) peptide (FIG. 4C). That the Act1 SEFIR domain CC' loop decoy peptide inhibited the Act1-IL-17RA interaction suggested that the peptide might also block IL-17 and IL-25 signaling. Indeed, it was found that the Act1 SEFIR domain CC' loop peptide, but not the Act1 SEFIR domain BB' loop peptide, partly attenuated IL-17- and IL-25-dependent signaling, as assessed by determining that amounts of phosphorylated IκB (pIκB), pJNK, phosphorylated extracellular signal-regulated kinase (pERK) and phosphorylated p38 mitogen-activated protein kinase (pp38 MAPK) by Western blotting (FIG. 4D). Moreover, the Act1 SEFIR domain CC' loop peptide attenuated IL-17-mediated expression of Cxcl1 (~50% inhibition) and IL-25-mediated expression of IL-13 Il13 (~60% inhibition), whereas the Act1 SEFIR domain BB' loop peptide had no effect (FIG. 4E). In addition, the CC' loop decoy peptide inhibited IL-17- and IL-25-dependent signaling and gene expression in a dose-and time-dependent manner (not shown).

Example 5

Figure 5:
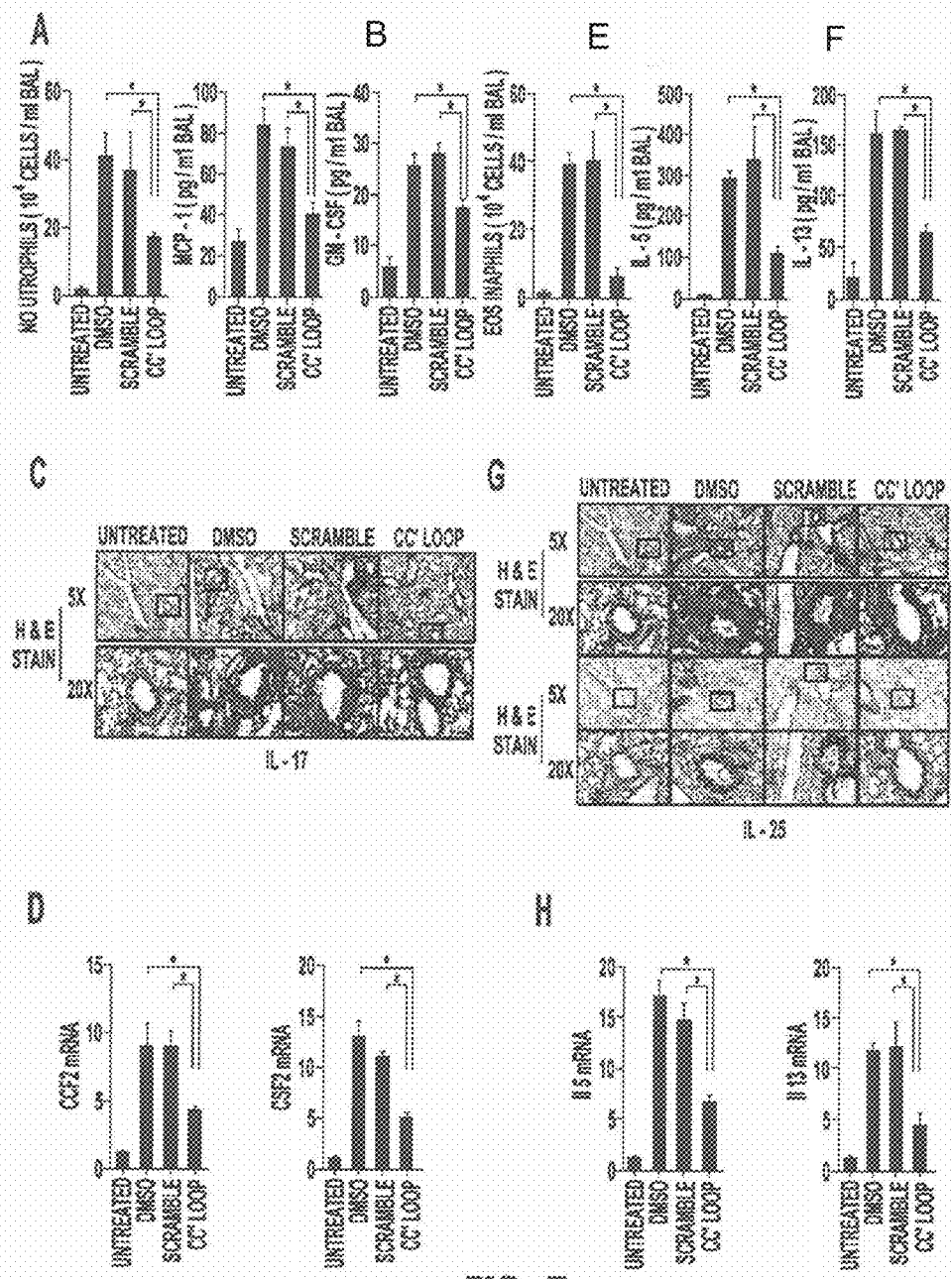
FIG. 5 provides bar graph and staining data showing that a cell-permeable CC' loop decoy peptide inhibits IL-17- and IL-25-induced pulmonary inflammation. Wild-type (WT) female BALB/c mice (n=4 mice per group) were pretreated with DMSO, scrambled peptide, or the CC' loop decoy peptide for 4 hours, after which they were administered saline, IL-17, or IL-25 intranasally. Mice were sacrificed and analyzed 16 hours after injection with IL-17 or 4 days after injection with IL-25.

The Cell-Permeable CC' Loop Decoy Peptide Inhibits IL-17- and IL-25-Induced Pulmonary Inflammation Because the Act1 SEFIR domain CC' loop decoy peptide disrupted the Act1-IL-17RA interaction and inhibited IL-17- and IL-25-dependent signaling in cultured cells, the inventors tested whether the peptide also blocked IL-17- and IL-25-dependent effector functions in vivo. It has been shown that Act1 plays an essential role in IL-17- and IL-25-mediated pulmonary inflammation. Thus, the inventors examined whether the Act1 SEFIR domain CC' loop decoy peptide ameliorated IL-17- and IL-25-induced airway inflammation in vivo. BALB/c mice were pretreated with scrambled peptide or with the Act1 SEFIR domain CC' loop decoy peptide for 4 hours, after which we injected the mice intranasally with IL-17 or IL-25. It was found that IL-17-induced neutrophilia and inflammation, as determined by measurement of neutrophil counts and the amounts of monocyte chemoattractant protein 1 (MCP-1, encoded by the gene Ccl2), a potent neutrophil-attracting chemokine, and granulocyte-macrophage colony-stimulating factor (GM-CSF, encoded by the gene Csf2) in the BAL fluid, were substantially reduced in mice treated with the CC' loop decoy peptide compared to those in mice pretreated with the scrambled peptide (FIG. 5, A and B). Consistently, IL-17-induced lung and airway recruitment of granulocytes was reduced in mice pretreated with the CC' loop decoy peptide compared to that in mice pretreated with the scrambled peptide (FIG. 5C). The lower grade of pulmonary inflammation in the mice treated with the CC' loop decoy peptide correlated with the decreased IL-17-dependent expression of genes encoding MCP-1 and GM-CSF in the lung tissues (FIG. 5D). Similarly, the Act1 SEFIR domain CC' loop decoy peptide substantially attenuated IL-25-induced eosinophilia and $T_H2$-type responses, as determined by measuring the numbers of eosinophils and the amounts of IL-5 and IL-13 in the BAL (FIG. 5. E and F). IL-25-induced lung and airway recruitment of granulocytes, predominantly eosinophils, as well as mucin production, as determined by Periodic acid-Schiff (PAS) staining, were reduced in mice pretreated with the CC' loop decoy peptide compared to that in mice pretreated with the scrambled peptide (FIG. 5G). The decreased pulmonary inflammation in Act1-deficient mice correlated with decreased expression of genes encoding the $T_H2$-type cytokines IL-5 and IL-13 in the lungs (FIG. 5H). Furthermore, the CC' loop decoy peptide inhibited IL-17- and IL-25-induced pulmonary inflammation in a dose-dependent manner (not shown). These results demonstrated that the Act1 SEFIR domain CC' loop decoy peptide played a protective role during IL-17- and IL-25-mediated pulmonary inflammation.

Example 6

The CC' Loop Motif is Common Among SEFIR Family Members

Figure 6:
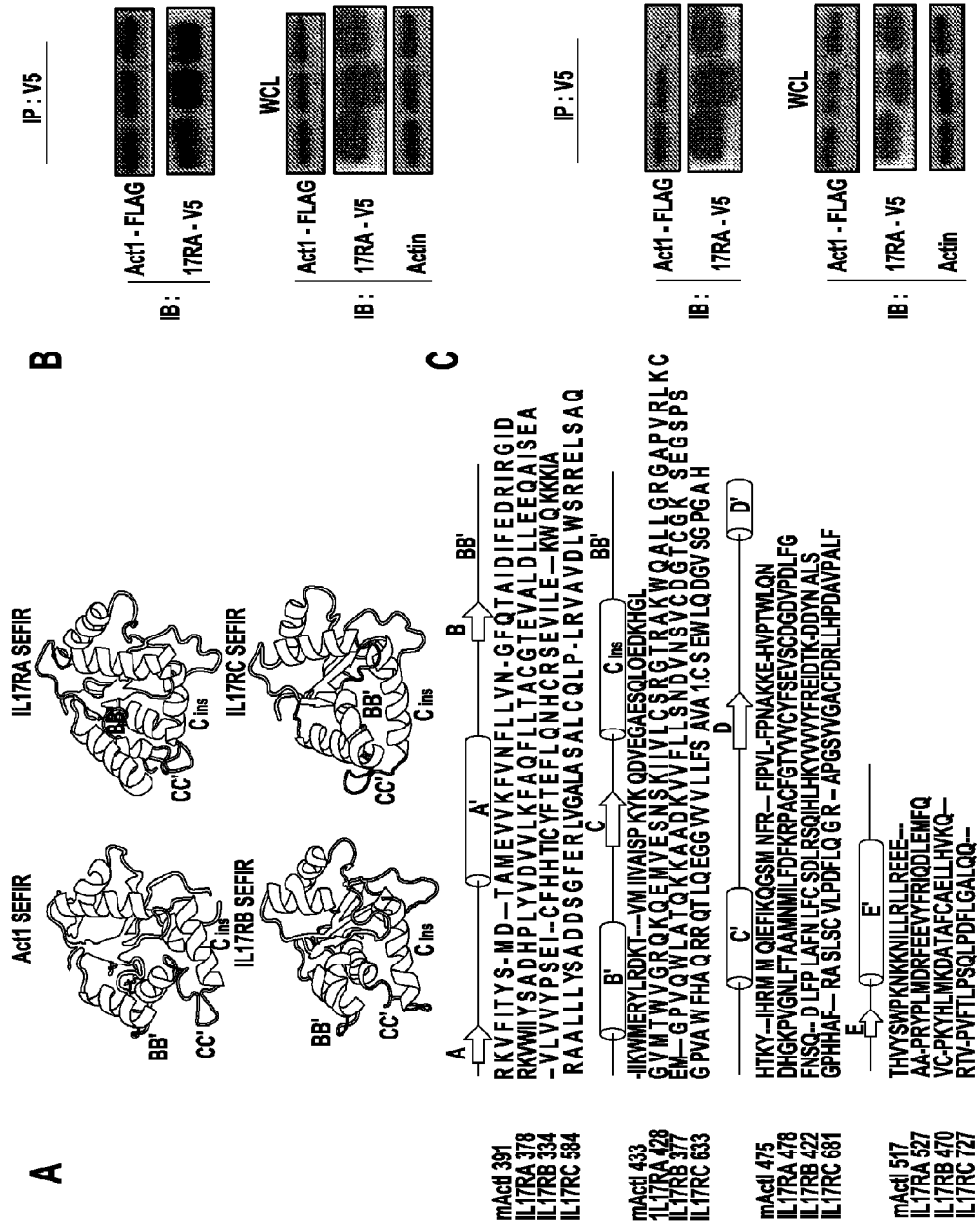
FIG. 6 provides data showing that the CC' loop motif is a common motif among SEFIR family members and is critical for SEFIR-SEFIR interactions.

Because the CC' loop of the Act1 SEFIR domain was critical for the interaction between Act1 and IL-17RA, the inventors investigated whether the CC' loop was present in the SEFIR domains of other SEFIR family members and whether it played similar roles. Homology models for the SEFIR domains of IL-17RA, IL-17RB, and IL-17RC were generated, as described earlier for modeling the SEFIR domain of Act1. It was found that the models of SEFIR domains from the IL-17Rs had similar structures, and each model had a BB' loop, a $C_{ins}$ helix, and a CC' loop as prominent features on the domain surface (FIG. 6A). The inventors then tested whether the CC' loop of the IL-17RA SEFIR domain was required for the interaction between the IL17-RA SEFIR domain and Act1. HeLa cells were cotransfected with plasmids encoding V5-tagged IL-17RA or the corresponding BB' loop (D-BB') or CC' loop (D-CC') deletion mutants of the receptor together with plasmid encoding FLAG-tagged Act1. The CC' loop deletion mutant of IL-17RA, exhibited a weaker interaction with Act1 than did the wild-type receptor, whereas the BB' loop mutant of IL-17RA retained the ability to interact with Act1 (FIG. 6B). Similar results were observed for mutants of IL-17RB (FIG. 6C). These results suggested that the CC' loop plays a conserved role, in multiple SEFIR family members, as a surface used for heterotypic SEFIR-SEFIR domain interactions.

Methods Used in Examples 1-6

Plasmids: Complementary DNA (cDNA) encoding FLAG-tagged mouse Act1 (mAct1) and its deletion and point mutants, including D-SEFIR1 to D-SEFIR5, 464LDE(→DRR), 467DEH(→RRD), 470GLH(→DDD), 473TKY(→ADA), D467R, E468R, H469D, G470D, L471D, H472D, T473A, K474D, and Y475A were subcloned into the plasmid pMSCV-IRES-GFP. cDNA encoding Myc-tagged mouse IL-17RB was also subcloned into pMSCV-IRES-GFP. cDNA encoding V5-tagged human IL-17RA and its mutants, D-BB' (residues 416 to 427 deleted) and D-CC' (residues 416 to 427 deleted), were subcloned into the vector pcDNA3.1. cDNA encoding V5-tagged mouse RB and its mutants D-BB' (residues 367 to 377 deleted) and D-CC' (residues 394 to 407 deleted) were subcloned into pcDNA3.1.

Cell culture and reagents: Primary MEFs were isolated from mouse embryos at day 14.5 as described previously. Qian, et al. Nat Immunol 8:247-256 (2007). Human embryonic kidney (HEK) 293 cells and HeLa cells were maintained in Dulbecco's modified Eagle's medium (DMEM) supplemented with 10% fetal bovine serum (FBS), penicillin G (100 μg/ml), and streptomycin (100 μg/ml). MEFs expressing IL-17RB were established by retroviral infection with pMSCV-IL-17RB-IRES-GFP. Recombinant IL-17 (IL-17A), IL-17E (IL-25) and tumor necrosis factor α (TNF-α) were purchased from R&D Systems. Protein A sepharose beads, FuGENE and protease inhibitor cocktail were obtained from Roche. An antibody against actin was purchased from Santa Cruz Biotechnology. Antibody against the FLAG tag (M2) was obtained from Sigma-Aldrich™. Antibody against the hemagglutinin (HA) tag was obtained from Covance. Trizol reagent and antibody against V5 were purchased from Invitrogen®. All peptides were synthesized by Biomatik. The cell-permeable peptides (with Antp sequence) were subject to N-terminal acetylation to increase their stability.

Expression and purification of IL-17RA and mAct1-SEFIR proteins: The cDNA encoding a SEFIR domain-containing fragment of human IL17RA (IL17RA-SEFIR, amino acid residues 351 to 616) was subcloned into a modified pET-28 vector, with a N-terminal 6×His tag (SEQ ID NO: 18)and a tobacco etch virus protease (TEV) recognition site (ENLYFQG) (SEQ ID NO: 21 )). The IL17RA SEFIR domain was expressed and purified by double-Nickel-Nitrilotriacetic Acid (Ni-NTA) affinity methods as previously described. Deng et al., Acta Crystallogr D Biol Crystallogr 60:203-204 (2004). The His-tag was subsequently removed from the eluted fusion protein by rTEV, and IL17RA-SEFIR was further purified as flow-through material from a second subtracting Ni-NTA column. Size-exclusion chromatography on a superdex s200 HR high resolution column was used as a final step for purification. The cDNA encoding a SEFIR domain containing a fragment of mouse Act1 (mAct1-SEFIR, residues 391 to 537) was subcloned into a modified pET28b vector that expresses maltose-binding protein (MBP) with an N-terminal 6×His tag (SEQ ID NO: 18) and a C-terminal TEV recognition site. Recombinant mAct1-SEFIR was expressed and purified as previously described. Deng et al., Proc Natl Acad Sci USA 105:1499-1504 (2008). The His-tagged MBP moiety was cleaved from the fusion protein by rTEV after the first Ni-NTA column purification. Recombinant mAct1-SEFIR was subsequently collected as flow-through from a second subtracting Ni-NTA column.

Modeling of the Act1 SEFIR domain: A homology model of the Act1 SEFIR domain was generated with 1-Tasser, based on an input sequence of human Act1 amino acid residues 399 to 574 (which correspond to residues 391 to 555 of mAct1) with no additional input information. Roy et al., Nat Protoc 5:725-738 (2010). Structures of TIR domains from TLR2, TLR4, TLR10, and MyD88 constituted most of the top ten templates selected by I-Tasser for homology modeling. Whereas the I-Tasser output C-scores suggested that the models were of modest quality, the top four models were very consistent with average root-mean-square deviations (Rmsd<1 Å). The model with the best C-score was energy minimized in CNS software package (Brunger, A. T. Nat Protoc 2:2728-2733 (2007)) and manually rebuilt to correct stereochemical errors and eliminate clashes with the software program COOT. Emsley et al., Acta Crystallogr D Biol Crystallogr 66:486-501 (2010). Homology models of the IL17RA, IL17RB, and IL17RC SEFIR domains were generated in a similar manner.

Transfection, retroviral infections and coimmunoprecipations: All transfections were conducted with FuGENE according to the manufacturer's instructions. For reconstitution assays in MEFs, cells were transinfecteddfected by retroviral infection supernatant as described previously. Qian et al., Nat Immunol 8:247-256 (2007). Briefly, viral supernatant was obtained by transfecting Phoenix cells with 5 μg of retroviral construct derived from pMSCV-IRES-GFP for 48 hours. MEFs were infected with viral supernatant for 24 hours and GFP-positive cells were sorted out to establish stable cell lines for downstream assay. For coimmunoprecipations, HeLa cells were transfected with FuGENE according to the manufacturer's instructions. Cell extracts were incubated with antibody (1 μg) and protein A beads (20 μl). After overnight incubation, beads were washed four times with lysis buffer, resolved by SDS-polyacrylamide gel electrophoresis (SDS-PAGE), and analyzed by Western blotting according to standard procedures. This method was also used in examples 7-11.

SPR analysis: Binding of purified Act1 SEFIR domain or peptides to IL-17RA was conducted on a Biacore 3000. Purified IL-17RA SEFIR domain was immobilized on a CM5 sensor chip in 10 mM acetic acid (pH 4.5). Purified Act1 SEFIR domain or peptides were allowed to flow over the chip in a buffer of 10 mM Hepes (pH 7.4), 150 mM NaCl, and 0.005% surfactant P20. The chip was regenerated with 1 M NaCl. Binding KD values were determined by Biaevaluation software.

Real-time polymerase chain reaction assays: Total RNA was extracted with Trizol reagent according to the manufacturer's instructions. The cDNAs were synthesized and real-time reverse transcription polymerase chain reaction (RT-PCR) assays were performed as described previously. Qian et al., Nat Immunol 8:247-256 (2007). This method was also used for examples 7-11.

Intranasal injection of mice with IL-17 and IL-25: Wild-type BALB/c female mice were pretreated with dimethyl sulfoxide (DMSO, the solvent for peptides), scrambled peptide, or the CC' loop decoy peptide for 4 hours, after which they underwent intranasal administration of saline, IL-17 (4 μg/mouse), or IL-25 (4 μg/mouse). For IL-25-treated mice, decoy peptides were administrated daily through intranasal injection after pretreatment. Mice were anesthetized with isoflurane and sacrificed. BAL fluid was collected 16 hours after injection with IL-17 or 4 days after injection with IL-25. A total of 0.7 ml of HL-1 medium (BioWhittaker®) was used to obtain BAL fluid through trachea with a blunt needle and a 1-ml syringe. Cytospin slide preparations were obtained with a Shandon CytoSpin III Cytocentrifuge (Shandon/Thermo Scientific). Differential leukocyte counts were obtained on cytospin slide preparations after incubation with Diff Quik Giemsa stain. Cytokines in the BAL were analyzed by MultipleX plate (Invitrogen®). H&E and PAS staining were performed on lung tissues after fixation in 10% neutral-buffered formalin and paraffin embedding to detect pulmonary inflammation and for assessment of goblet cell metaplasia and mucin accumulation in airway epithelial cells.

Statistical analyses: Statistical analyses were performed by one-way analysis of variance (ANOVA), followed by multiple pair-wise comparisons of the treatments, or by the Student's t test, where appropriate.

Example 7

The Structure of IL-17RB-SEFIR

Figure 8:
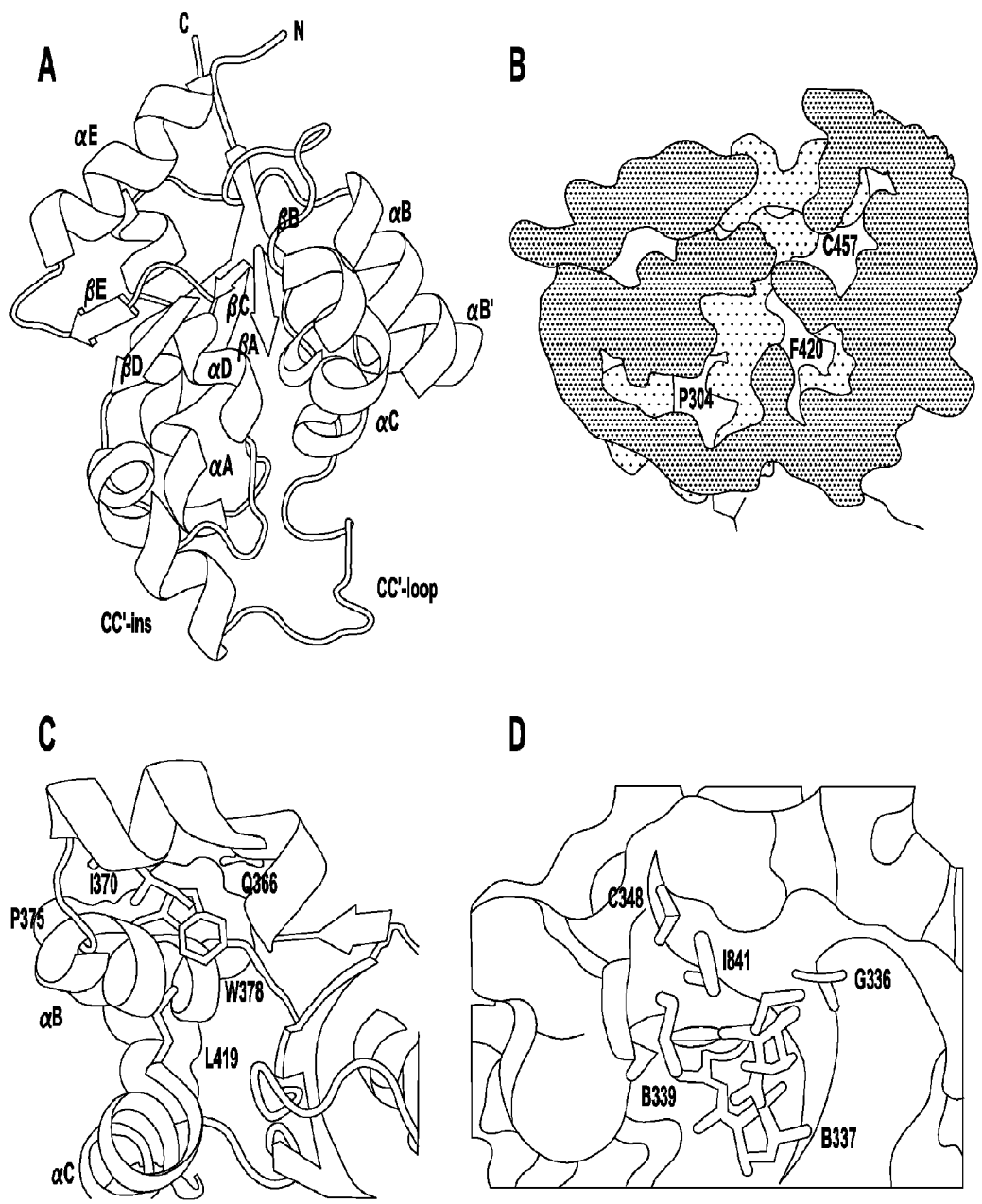
FIG. 8 provides computer modeling representations of the structure of IL-17RB-SEFIR.

The IL-17RB-SEFIR structure, representing the first structure of any SEFIRs, displays a compact globular architecture comprised of a five-stranded (βA to βE) parallel β-sheet that is wrapped by six helices (αA, αB', αB, αC, αD and αE, FIG. 8A) with loops of various lengths connecting the secondary structures (the individual loop that connects the β-strand and its next neighboring helix is termed after the name of the secondary structures, i.e., the DD' loop connects strand βD and helix αD). The structure is well defined except for a 20 amino acids (A.A.) region connecting strand βC and helix αC (residues 396-416, we named as CC' segment), the electron density of which is not observable. To evaluate if the missing density was due to proteolysis during crystallization, the crystals were analyzed used for data collection and found by SDS-PAGE that the protein in the crystal was intact, suggesting a conformational disorder instead of degradation of the material. There are two topological possibilities for connecting residues 396 to 416. One scenario is to crossover the DD' loop from its outer surface, forming a knot topology. Alternatively, residues 396 to 416 could thread inwards and through the DD' loop from the inner side toward the protein core. However, after carefully analyzing the structure, the latter alternative was found to be not feasible. In particular, the side chains of the residues located in the DD' loop pack tightly, leaving no space for accommodating a peptide chain to go through the DD' loop (FIG. 8B). Specifically, L393, P394, F420, L450, Y454 and L457 are forming a tightly packed hydrophobic core with close non-bonding atom-to-atom distance for van der Waals interactions (i.e., the distance of L450 Cδ1 to Y454 Cδ2 is 4.5 Å). Therefore, the enclosed space within DD' loop is fully occupied, prohibiting the CC' segment to go through. Using Falc-loop Modeling Server (Lee et al., Proteins 78: 3428-3436 (2011)), the missing CC' segment was modeled containing two portions, a helix insertion (CC'-ins) and a loop (CC'-loop) (FIG. 8A), which is consistent with the secondary structures defined in the inventors previous homology-modeled IL-17RB-SEFIR based on a TIR template. In the current structure, there is a short helix αB' (residue 363-373) in the linkage between helix αB and strand βB, which is nearly perpendicular to helix αB. Helix αB' is tethered to its helices 'B and 'C through hydrophobic interactions between residue I370 on helix αB' and a hydrophobic platform comprised of residues P375, W378 on helix αB and L419 on helix αC (FIG. 8C). In addition, residue W378 on helix αB of IL-17RB is hydrogen bonded to Q366 on αB' (distance of atom Nε1 of W378 and atom Oε1 of Q366 is 2.8 Å), which further stabilizes and locks αB' and αB helices into a rigid conformation. Residue W378 is strictly conserved among SEFIR containing IL-17Rs and Act1. Residues equivalent to IL-17RB Q366 are either a glutamate or serine in other SEFIR proteins. The helix αB' appears to carry a unique role in SEFIR mediated IL-17 signaling.

Example 8

Key IL-17RB Residues for Act1 Interaction are Located on Helix αC

Figure 9:
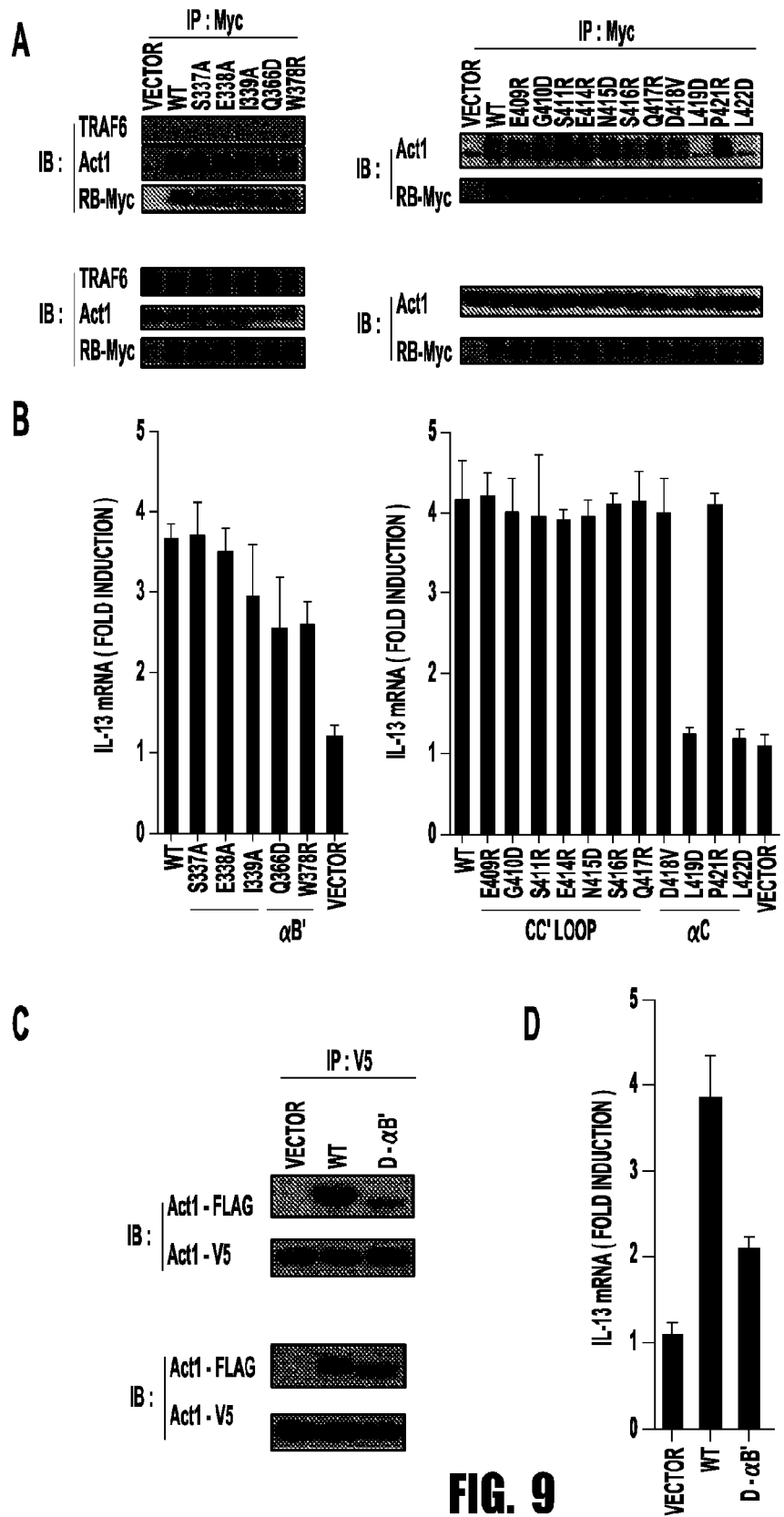
FIG. 9 provides bar graphs and Western blots showing the results of mutagenesis and Co-IP studies on IL-17RB-SEFIR.
Figure 10:
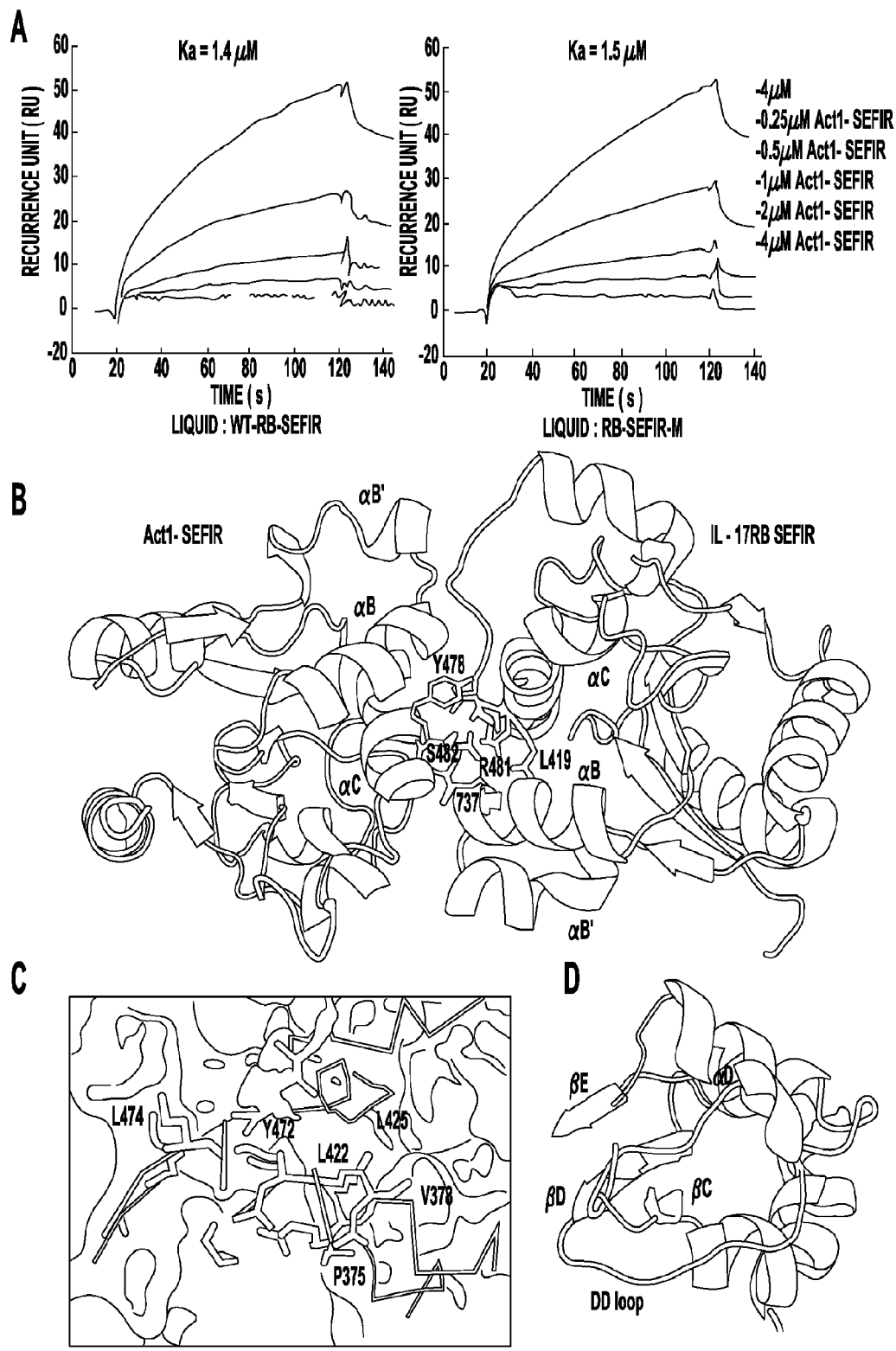
FIG. 10 provides line graphs and computer modeling results of the SEFIR-mediated Act1:IL-17RB interaction.

The adaptor protein Act1 mediates IL-17RB signaling in a SEFIR-dependent manner, via hetero-dimerization of Act1 and IL-17RB. Swaidani et al., Journal of immunology 182: 1631-1640 (2009). The deletion of SEFIR domain from either protein abolished their interactions. In the current study, a direct interaction between the SEFIR domains from IL-17RB and Act1 was detected using Surface Plasmon Resonance (SPR, FIG. 10A). The crystallized mutant of IL-17RB harboring alanine substitutions at four lysine residues (K364, K367, K368 and K369) on helix αB' had no obvious impact on the ability of IL-17RB-SEFIR to interact with Act1-SEFIR (FIG. 10A). To identify residues on IL-17RB-SEFIR that are key to its function, 16 mutants of IL-17RB-SEFIR were generated and reconstitution and CO-IP experiments were performed in MEFs that lack IL-17RB expression. The mutation sites are grouped into following four regions: 1) putative TRAF6 motif (S337A, E338A and I339A); 2) CC' loop (E409R, G410D, S411R, E414R, N415D, S416R and Q417R); 3) αC (D418V, L419D, P421R and L422D); 4) αB' (Q366D and W378R). The inventors found mutations of Q366D and W378R on IL-17RB-SEFIR only partly decreased its interaction with Act1, and attenuated the gene expression stimulated by IL-25 (FIGS. 9A and B). In contrast, single mutation of L419D or L422D of IL-17RB completely abolished the interactions with Act1 and gene expression. Both L419 and L422 are located on the surface of αC helix and solvent accessible, implying their potential roles in protein interactions. Interestingly, all other mutations did not show significant effects, including the point mutations of CC' loop. The inventors previously showed that the CC'-deletion mutant of IL-17RB displayed decreased interaction with Act1. However, the structure of IL-17RB-SEFIR now suggests that the loss of function by the CC'-deletion mutant of IL-17RB exhibited in the previous studies might be actually due to perturbation of the structural folding. Therefore, the results here implicated that αC helix of IL-17RB is the most critical region for its heterotypic interaction with Act1.

Example 9

Key Act1 Residues for IL-17R Interactions are Also Located on Helix αC

The structural information of IL-17RB-SEFIR allows us again to reassess the functional data on Act1-SEFIR that we reported recently. As shown in Examples 1-6, four residues on Act1-SEFIR were identified where single A.A. substitutions (L474D, H475D, K477D and Y478A within sequence of LDEDEHGLIITKY (SEQ ID NO: 5), with L474, H475, K477 and Y478 highlighted) were shown to abolish the interactions with IL-17RA and could not restore IL-17A- and IL-17E (IL-25)-mediated gene expression in Act1$^{-/-}$ MEFs, suggesting these residues as critical for heterotypic SEFIR-SEFIR interactions. In addition, it was shown that a cell-permeable peptide derived from mAct1-SEFIR (containing LDEDEHGLHTKY (SEQ ID NO: 5)) disrupts the Act1-IL-17RA interaction and inhibits IL-17- and IL-25-dependent signaling. To be noted, these residues were modeled to situate on the C-terminal end of the CC' loop in the previously homology-modeled structure, which was based on a distantly related TIR template. Therefore, earlier experiments indicated this peptide to be a CC' loop decoy. To obtain better structural insights, the inventors remodeled the structure of mAct1 based on the high-resolution crystal structure of IL-17RB-SEFIR. Based on the crystal structure of IL-17RB-SEFIR, the structure of mouse Act1 was remodeled by homology modeling using SWISS-Model interface. Arnold et al, Bioinformatics (Oxford, England) 22: 195-201 (2006). All four key residues (L474, H475, K477 and Y478)

are now identified as being present on the N-terminal segment of αC helix. Residues L474, K477 and Y478 are exposed to solvent, while H475 is partially exposed, suggesting their potential roles in interactions with other SEFIR domains from IL-17 receptors. Collectively, the structural and functional data from IL-17RB and Act1 SEFIR domains suggest that αC helices in both proteins serve as the 'hot spot' for heterotypic SEFIR-SEFIR interactions. In addition, structure based family sequence alignment shows that αC helix is also conserved in IL-17RA and RC, suggesting this helix is a common structural signature for IL-17 receptor signaling.

Example 10

A Model for IL-17RB:Act1 Heterotypic SEFIR Complex

The inventors then constructed a model of Act1-SEFIR:IL-17RB-SEFIR hetero-dimer complex by using HAD-DOCK server. de Vries et al., Nature protocols 5: 883-897 (2010). In this model, the interactions between Act1 and IL-17RB-SEFIR domains are predominantly clustered at helix αC and the tip of helix αB (FIG. 10B). The αB and αC helices from IL-17RB-SEFIR domain are almost perpendicular to their counterparts in Act1, forming a four-helix bundle at the interface, involving hydrophobic and charge-charge interactions. Specifically, residue I434 (αB), the aliphatic side chain of residue R481 and residues M482 (αC) of Act1 are stacked on a hydrophobic groove on the surface of IL-17RB-SEFIR, comprised of residues P375, V376 from αB and L422 and L426 from αC, involving extensive hydrophobic interactions (FIG. 10C). Y478 of Act1 is also abutting this hydrophobic platform with its edges. The basic residues K477 and R481 are forming favorable interactions with a negatively charged patch on the surface of IL-17RB-SEFIR, contributed mainly by two acidic residues, E414 and D418. The model of Act1-IL-17RB heterodimer suggests K477 and Y478 of Act1 as important residues for mediating heterotypic SEFIR-SEFIR interactions, which agrees with the data on the interaction of Act1 with IL-17RA provided in Examples 1-6. L474 and H475 of Act1 however do not appear from this model to contribute much to the binding of Act1 to IL-17RB, suggesting their possible roles perhaps related to receptor binding specificity since these residues were found as critical for IL-17RA binding and signaling.

Example 11

Homotypic SEFIR-SEFIR Association via αB' Helix

The exact stoichiometry and detailed mechanism by which SEFIR domain containing proteins associate with each other are not known. The inventors have found purified IL-17RB-SEFIR displays as predominantly monomeric in solution, based on size exclusion chromatography and dynamic light scattering. It is also a monomer in the crystal structure as considered by PISA server. Krissinel et al., J Mol Biol 372: 774-797 (2007). However, Act1 was shown to form homo-dimer or homo-oligomers through its SEFIR domain. Mauro et al., Biochemical and biophysical research communications 309: 84-90 (2003). The earlier examples show that the homo-association of Act1 was not affected by CC'-deletion or site mutations in CC' loop that are deleterious to IL-17 signaling. However, later studies found the deletion of the helix αB' (D-BB', residues 425-432 deleted) in Act1-SEFIR domain greatly reduced its homotypic interaction and IL-17E (IL-25)-mediated gene expression. (FIGS. 9C and D). The cumulative data from these studies suggest that Act1 self-association is required for IL-17E (IL-25) signaling and this homotypic interaction is mediated through helix αB' in the SEFIR domain (corresponding to the key structural motif BB' loop in TIR domains). This hypothesis is consistent with the modeled heterotypic complex of Act1 and IL-17RB. In this model, the αB' helices from both Act1 and IL-17RB SEFIR domains are located distal to the four-helix bundle core that is comprised of αB/αC helices from both proteins, in a back-to-back fashion, not participating in any direct interactions at the hetero dimer interface. However the αB' helices from both proteins are largely exposed, suggesting they could be potentially involved in homo-dimerization of SEFIR domains.

Methods used in Examples 7-11

Protein Expression and Purification. The mouse IL-17RB-SEFIR (amino acid residues 314 to 486) was cloned into a modified pET28 vector, as a SUMO fusion protein with a N-terminal 6×His tag.(SEQ ID NO: 18) The IL-17RB-SEFIR domain was expressed and purified using similar protocol as previously described (13), however using protease Ulp1 for removing the His-tagged SUMO moiety. Krumm et al., Proc Natl Acad Sci USA 105: 20711-20715 (2008). The purified protein failed in our crystallization trials. Limited proteolysis by chymotrypsin and subsequent peptide sequencing was used in aiding the design of a new stable construct (325-486). Residues K364, K367, K368 and K369 were additionally mutated to alanines to reduce surface entropy. Derewenda et al., Acta Crystallogr D Biol Crystallogr 62: 116-124 (2006). This mutant protein crystallized successfully. Mouse Act1-SEFIR protein was purified as described herein.

Crystallization, data collection and structure determination. IL-17RB-SEFIR crystallized in a condition containing 0.2 M sodium acetate, pH 5.0, 1.6 M Ammonium citrate dibasic. 20% glycerol was added to the mother liquid as cryoprotectant. A set of data was collected on a SeMet substituted crystal at beamline 19-ID at the Advanced Photon Source, Argonne National Laboratory. The structure was solved by Single Wavelength Anomalous Dispersion method using HKL3000. Minor et al., Acta Crystallogr D Biol Crystallogr 62: 859-866 (2006). The SeMet phased model was used to solve the native structure by molecular replacement method using phaser. McCoy et al., J. Appl. Cryst. 40: 658-674 (2007). PHENIX program (Adams et al., Acta Crystallogr D Biol Crystallogr 66: 213-221) was used for refinement and Coot (Emsley, P. a. C., K., Acta Crystallogr D Biol Crystallogr. 60: 2126-2132 (2004)) was used for iterative manual model building. Translation, libration and screw-rotation displacement (TLS) groups used in the refinement were defined by the TLMSD server. Painter et al., Acta Crystallogr D Biol Crystallogr 62: 439-450 (2006). The final structure was refined to 1.8 Å resolution and crystallographic $R_{work}$ and $R_{free}$ are 18.0% and 22.3%, respectively. The final protein model has 97.0% of all residues residing in the most-favored region of the Ramachandran plot and 3.0% in additionally allowed region, as calculated by Molprobity. Chen et al., Acta Crystallogr D Biol Crystallogr 66: 12-21 (2010). All molecular graphic figures were generated with PYMOL. DeLano, W. L. 2002. The PyMOL Molecular Graphics System, available online at pymol.org.

Surface plasmon resonance (SPR) analysis. Binding between analytes (mouse Act1-SEFIR) and ligands [wild type IL-17RB-SEFIR (WT-RB-SEFIR), the crystallized mutant IL-17RB-SEFIR (RB-SEFIR-M)] was conducted on a Biacore 3000. The ligands were immobilized on a CM5 sensor chip in 10 mM acetic acid (pH 4.5 or pH 5.0). The analytes were allowed to flow over the chip in a buffer of 10 mM Hepes (pH 7.4), 150 mM NaCl, and 0.005% surfactant P20. The chips were regenerated with 1 M NaCl or 0.05% SDS. Binding KD values were determined by Biaevaluation software.

Cell culture, plasmids and antibodies. MEFs and HeLa cells were maintained in Dulbecco's modified Eagle's medium (DMEM) supplemented with 10% fetal bovine serum (FBS), penicillin G (100 μg/ml), and streptomycin (100 μg/ml). MEFs expressing IL-17RB were established by retroviral infection with pMSCV-IL-17RB-IRES-GFP. Complementary DNA (cDNA) encoding Myc-tagged mouse IL-17RB and its point mutants were subcloned into the plasmid pMSCV-IRES-GFP. cDNA encoding Myc-tagged mouse IL-17RB was also subcloned into pMSCV-IRES-GFP. cDNA encoding V5-tagged mouse Act1 (mAct1) were subcloned into the vector pcDNA3.1. cDNA encoding FLAG-tagged mouse Act1 and its mutants, D-BB'(residues 425-432 deleted) and point mutant H472D were subcloned into the plasmid pMSCV-IRES-GFP.

Example 13

ASI Peptide Inhibits Inflammation

Figure 11:
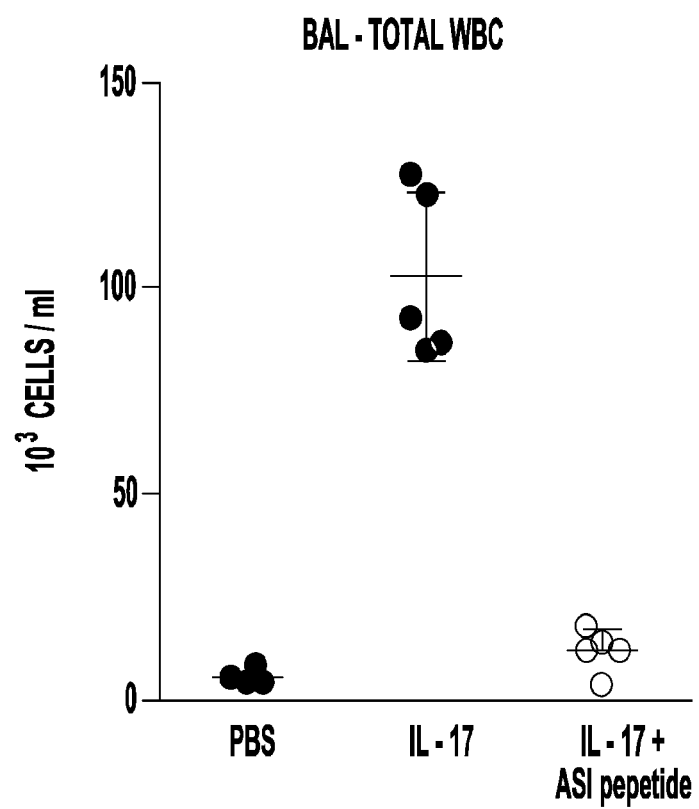
FIG. 11 provides a graph showing that the ASI peptide inhibits inflammation in a murine model of experimental House Dust Mite (HDM)-induced Asthma. The white blood cell count was about 100,000 cells/ml when IL-17 was used alone, but dropped to about 10,000 cells/ml when ASI peptide was used together with IL-17.
Figure 12:
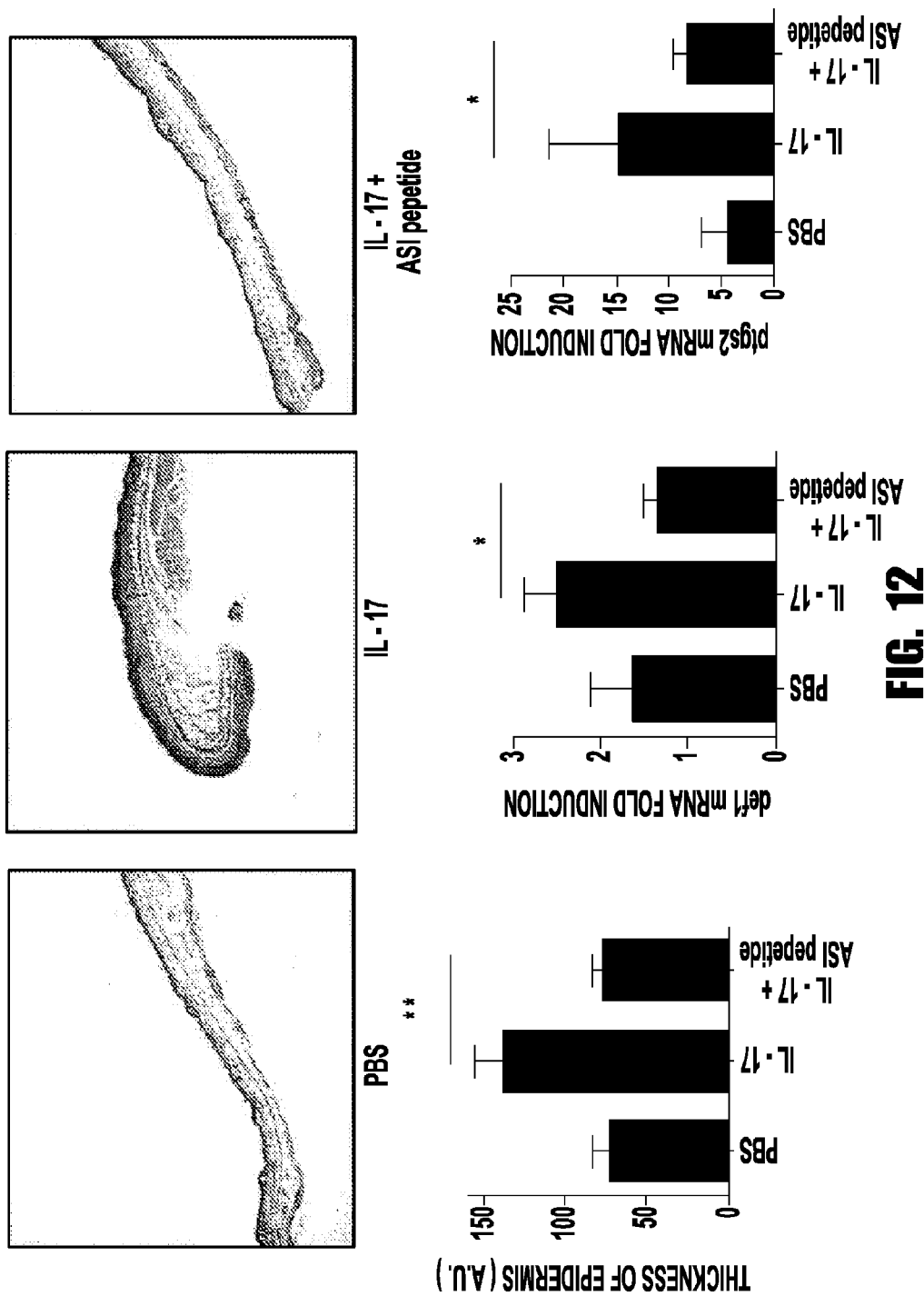
FIG. 12 provides staining images and bar graphs showing that the AS1 peptide inhibits IL-17-induced inflammation in mouse ear skin. In the staining images, the slide showing IL-17 alone exhibited an increased thickness of epidermis, indicating epidermal hyperplasia and inflammation, whereas the other slides showed normal, thinner epidermis and a lack of inflammation. The bar graphs consistently show that addition of the ASI peptide counteracted the inflammatory results of IL-17.

Experiments were carried out to demonstrate that the ASI peptide (the CC' loop decoy peptide (SEQ ID NO: 5) inhibits inflammation. FIG. 11 shows that the ASI peptide inhibits inflammation in a murine model of experimental House Dust Mite (HDM)-induced Asthma. Asthma was induced by daily intranasal administration of PBS, HDM with or without ASI HDM (25 μg) or saline in a volume of 20 μl for 5 days each week. On day 6, total white blood (WBC) were counted in bronchoalveolar lavage (BAL) samples. FIG. 12 provides staining images and bar graphs showing the results of experiments carried out to show that the ASI peptide inhibits IL-17-induced inflammation in mouse ear skin. Ears from C57B1/6 mice (n=3 for each group) were injected daily with PBS, IL-17 with or without ASI. On day 7, ears were collected for staining with H&E and real-time analysis of gene expression.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A decoy peptide consisting of less than about 50 amino acids substantially homologous to at least a portion of the amino acid sequence of the αC helix region of the SEFIR domain of Act 1 and comprising the amino acid sequence HGLHXKY (SEQ ID NO: 1), wherein the decoy peptide competitively inhibits the binding of interleukin-17 receptor (IL-17R) to adaptor protein nuclear factor κB activator 1 (Act 1).

2. The decoy peptide of claim 1, wherein the decoy peptide comprises the amino acid sequence HGLHTKY (SEQ ID NO: 4).

3. The decoy peptide of claim 1, wherein the decoy peptide comprises the amino acid sequence LDEDEHGLHTKY (SEQ ID NO: 5).

4. The decoy peptide of claim 1, wherein the decoy peptide further comprises a protein transduction domain.

5. The decoy peptide of claim 4, wherein the protein transduction domain is derived from antennapedia.

6. The decoy peptide of claim 4, wherein the protein transduction domain has the amino acid sequence DRQIKIWFQNRRMKWKK (SEQ ID NO: 11).

7. The decoy peptide of claim 4, wherein the decoy peptide has the amino acid sequence DRQIKIWFQNRRMKWKKLDEDEHGLHTKY (SEQ ID NO: 17).

8. A method of treating an interleukin-17 (IL-17) mediated disease in a subject, comprising administering to the subject having the interleukin-17 mediated disease a therapeutically effective amount of the decoy peptide of claim 1.

9. The method of claim 8, wherein the decoy peptide comprises the amino acid sequence HGLHTKY (SEQ ID NO: 4).

10. The method of claim 8, wherein the decoy peptide comprises the amino acid sequence LDEDEHGLHTKY (SEQ ID NO: 5).

11. The method of claim 8, wherein the decoy peptide further comprises a protein transduction domain.

12. The method of claim 11, wherein the protein transduction domain is derived from antennapedia.

13. The method of claim 12, wherein the protein transduction domain has the amino acid sequence DRQIKIWFQNRRMKWKK (SEQ ID NO: 11).

14. The method of claim 13, wherein the decoy peptide has the amino acid sequence DRQIKIWFQNRRMKWKKLDEDEHGLHTKY (SEQ ID NO: 17).

15. The method of claim 8, wherein the IL-17 mediated disease is an inflammatory disease or an autoimmune disease.

16. The method of claim 15, wherein the IL-17 mediated disease is an inflammatory disease selected from the group consisting of asthma, inflammatory bowel disease, multiple sclerosis, experimental autoimmune encephalomyelitis, and allergen-induced pulmonary inflammation.

17. The method of claim 16, wherein the disease is asthma.

18. The method of claim 15, wherein the IL-17 mediated disease is an autoimmune disease selected from the group consisting of systemic lupus erythematosus, rheumatoid arthritis, allograft rejection, drug-induced lupus and psoriasis.

19. The method of claim 8, wherein the IL-17 is IL-17A.

20. The method of claim 8, wherein the IL-17 is IL-17E.

* * * * *

UNITED STATES PATENT AND TRADEMARK OFFICE
CERTIFICATE OF CORRECTION

PATENT NO. : 9,611,295 B2
APPLICATION NO. : 14/354608
DATED : April 4, 2017
INVENTOR(S) : Xiaoxia Li et al.

It is certified that error appears in the above-identified patent and that said Letters Patent is hereby corrected as shown below:

In the Specification

Column 1, Line 16, please insert the following paragraph:
--This invention was made with government support under HL098935, NS071998 and HL103453 awarded by the National Institutes of Health. The government has certain rights in the invention.--

Signed and Sealed this
Twenty-seventh Day of September, 2022

Katherine Kelly Vidal
*Director of the United States Patent and Trademark Office*

SEQUENCE LISTING

```
<160> NUMBER OF SEQ ID NOS: 37

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 1

His Gly Leu His Xaa Lys Tyr
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Any amino acid

<400> SEQUENCE: 2

Asp Leu Phe Xaa Xaa Ala
1               5

<210> SEQ ID NO 3
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 3

Val Tyr Pro Ser Glu Ile Cys Phe
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Gly Leu His Thr Lys Tyr
1               5

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Asp Glu Asp Glu His Gly Leu His Thr Lys Tyr
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Asp Leu Phe Pro Leu Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Asp Leu Phe Thr Ala Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Asp Ala Leu Ala Ala Trp
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

His Asp Ala Phe Arg Ala Ser Leu Ser
1               5

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Arg Lys Lys Arg Arg Gln Arg Arg Arg Pro Pro Gln
1               5                   10

<210> SEQ ID NO 11
<211> LENGTH: 17
<212> TYPE: PRT
<213> ORGANISM: Drosophila sp.

<400> SEQUENCE: 11

Asp Arg Gln Ile Lys Ile Trp Phe Gln Asn Arg Arg Met Lys Trp Lys
1               5                   10                  15

Lys

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Arg Met Lys Trp Lys Lys
1               5

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Gly Gly Arg Leu Ser Tyr Ser Arg Arg Phe Ser Thr Ser Thr
1               5                   10                  15

Gly Arg

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 14

Arg Arg Leu Ser Tyr Ser Arg Arg Arg Phe
1               5                   10

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gly Gly Arg Leu Ala Tyr Leu Arg Arg Arg Trp Ala Val Leu Gly
1               5                   10                  15

Arg

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Arg Arg Arg Arg Arg Arg Arg
1               5

<210> SEQ ID NO 17
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Arg Gln Ile Lys Ile Trp Phe Gln Asn Arg Arg Met Lys Trp Lys
1               5                   10                  15

Lys Leu Asp Glu Asp Glu His Gly Leu His Thr Lys Tyr
            20                  25

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 18

His His His His His His
1               5

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Pro Lys Tyr Lys Gln Asp Val Glu Gly Ala Glu Ser Gln

```
                          1               5                   10
```

<210> SEQ ID NO 20
<211> LENGTH: 8
<212> TYPE: PRT
<213> ORGANISM: Mus sp.

<400> SEQUENCE: 20

```
Glu Asp Arg Ile Arg Gly Ile Asp
1               5
```

<210> SEQ ID NO 21
<211> LENGTH: 7
<212> TYPE: PRT
<213> ORGANISM: Tobacco etch virus

<400> SEQUENCE: 21

```
Glu Asn Leu Tyr Phe Gln Gly
1               5
```

<210> SEQ ID NO 22
<211> LENGTH: 148
<212> TYPE: PRT
<213> ORGANISM: Mus sp.

<400> SEQUENCE: 22

```
Arg Lys Val Phe Ile Thr Tyr Ser Met Asp Thr Ala Met Glu Val Val
1               5                   10                  15

Lys Phe Val Asn Phe Leu Leu Val Asn Gly Phe Gln Thr Ala Ile Asp
            20                  25                  30

Ile Phe Glu Asp Arg Ile Arg Gly Ile Asp Ile Ile Lys Trp Met Glu
        35                  40                  45

Arg Tyr Leu Arg Asp Lys Thr Val Met Ile Ile Val Ala Ile Ser Pro
    50                  55                  60

Lys Tyr Lys Gln Asp Val Glu Gly Ala Glu Ser Gln Leu Asp Glu Asp
65                  70                  75                  80

Glu His Gly Leu His Thr Lys Tyr Ile His Arg Met Met Gln Ile Glu
                85                  90                  95

Phe Ile Ser Gln Gly Ser Met Asn Phe Arg Phe Ile Pro Val Leu Phe
            100                 105                 110

Pro Asn Ala Lys Lys Glu His Val Pro Thr Trp Leu Gln Asn Thr His
        115                 120                 125

Val Tyr Ser Trp Pro Lys Asn Lys Lys Asn Ile Leu Leu Arg Leu Leu
    130                 135                 140

Arg Glu Glu Glu
145
```

<210> SEQ ID NO 23
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Asp Arg Gln Ile Lys Ile Trp Phe Gln Asn Arg Arg Met Lys Trp Lys
1               5                   10                  15

Lys Glu Asp Arg Ile Arg Gly Ile Asp
            20                  25
```

<210> SEQ ID NO 24
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Asp Arg Gln Ile Lys Ile Trp Phe Gln Asn Arg Arg Met Lys Trp Lys
1               5                   10                  15
Lys Tyr Glu Leu Gly Thr Glu Thr His Asp Lys
            20                  25

<210> SEQ ID NO 25
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Asp Arg Gln Ile Lys Ile Trp Phe Gln Asn Arg Arg Met Lys Trp Lys
1               5                   10                  15
Lys Leu Asp Glu Asp Glu His Gly Leu Asp Thr Lys Tyr
            20                  25

<210> SEQ ID NO 26
<211> LENGTH: 166
<212> TYPE: PRT
<213> ORGANISM: Homo sapiens

<400> SEQUENCE: 26

Arg Lys Val Trp Ile Ile Tyr Ser Ala Asp His Pro Leu Tyr Val Asp
1               5                   10                  15
Val Val Leu Lys Phe Ala Gln Phe Leu Leu Thr Ala Cys Gly Thr Glu
            20                  25                  30
Val Ala Leu Asp Leu Leu Glu Glu Gln Ala Ile Ser Glu Ala Gly Val
        35                  40                  45
Met Thr Trp Val Gly Arg Gln Lys Gln Glu Met Val Glu Ser Asn Ser
    50                  55                  60
Lys Ile Ile Val Leu Cys Ser Arg Gly Thr Arg Ala Lys Trp Gln Ala
65                  70                  75                  80
Leu Leu Gly Arg Gly Ala Pro Val Arg Leu Arg Cys Asp His Gly Lys
                85                  90                  95
Pro Val Gly Asn Leu Phe Thr Ala Ala Met Asn Met Ile Leu Phe Asp
            100                 105                 110
Phe Lys Arg Pro Ala Cys Phe Gly Thr Tyr Val Val Cys Tyr Phe Ser
        115                 120                 125
Glu Val Ser Cys Asp Gly Asp Val Pro Asp Leu Phe Gly Ala Ala Pro
    130                 135                 140
Arg Tyr Pro Leu Met Asp Arg Phe Glu Glu Val Tyr Phe Arg Ile Gln
145                 150                 155                 160
Asp Leu Glu Met Phe Gln
                165

<210> SEQ ID NO 27
<211> LENGTH: 151
<212> TYPE: PRT

<213> ORGANISM: Homo sapiens

<400> SEQUENCE: 27

Val Leu Val Val Tyr Pro Ser Glu Ile Cys Phe His His Thr Ile Cys
1               5                   10                  15

Tyr Phe Thr Glu Phe Leu Gln Asn His Cys Arg Ser Glu Val Ile Leu
            20                  25                  30

Glu Lys Trp Gln Lys Lys Ile Ala Glu Met Gly Pro Val Gln Trp
        35                  40                  45

Leu Ala Thr Gln Lys Lys Ala Ala Asp Lys Val Val Phe Leu Leu Ser
    50                  55                  60

Asn Asp Val Asn Ser Val Cys Asp Gly Thr Cys Gly Lys Ser Glu Gly
65                  70                  75                  80

Ser Pro Ser Glu Asn Ser Gln Asp Leu Phe Pro Leu Ala Phe Asn Leu
                85                  90                  95

Phe Cys Ser Asp Leu Arg Ser Gln Ile His Leu His Lys Tyr Val Val
            100                 105                 110

Val Tyr Phe Arg Glu Ile Asp Thr Lys Asp Tyr Asn Ala Leu Ser
        115                 120                 125

Val Cys Pro Lys Tyr His Leu Met Lys Asp Ala Thr Ala Phe Cys Ala
    130                 135                 140

Glu Leu Leu His Val Lys Gln
145                 150

<210> SEQ ID NO 28
<211> LENGTH: 156
<212> TYPE: PRT
<213> ORGANISM: Homo sapiens

<400> SEQUENCE: 28

Arg Ala Ala Leu Leu Tyr Ser Ala Asp Asp Ser Gly Phe Glu Arg
1               5                   10                  15

Leu Val Gly Ala Leu Ala Ser Ala Leu Cys Gln Leu Pro Leu Arg Val
            20                  25                  30

Ala Val Asp Leu Trp Ser Arg Arg Glu Leu Ser Ala Gln Gly Pro Val
        35                  40                  45

Ala Trp Phe His Ala Gln Arg Arg Gln Thr Leu Gln Glu Gly Gly Val
    50                  55                  60

Val Val Leu Leu Phe Ser Pro Gly Ala Val Ala Leu Cys Ser Glu Trp
65                  70                  75                  80

Leu Gln Asp Gly Val Ser Gly Pro Gly Ala His Gly Pro His Asp Ala
                85                  90                  95

Phe Arg Ala Ser Leu Ser Cys Val Leu Pro Asp Phe Leu Gln Gly Arg
            100                 105                 110

Ala Pro Gly Ser Tyr Val Gly Ala Cys Phe Asp Arg Leu Leu His Pro
        115                 120                 125

Asp Ala Val Pro Ala Leu Phe Arg Thr Val Pro Val Phe Thr Leu Pro
    130                 135                 140

Ser Gln Leu Pro Asp Phe Leu Gly Ala Leu Gln Gln
145                 150                 155

<210> SEQ ID NO 29
<211> LENGTH: 157
<212> TYPE: PRT
<213> ORGANISM: Mus sp.

<400> SEQUENCE: 29

```
Leu Leu Pro Leu Ile Lys Val Leu Val Val Tyr Pro Ser Glu Ile Cys
1               5                   10                  15

Phe His His Thr Val Cys Arg Phe Thr Asp Phe Leu Gln Asn Tyr Cys
            20                  25                  30

Arg Ser Glu Val Ile Leu Glu Lys Trp Gln Lys Lys Ile Ala Glu
        35                  40                  45

Met Gly Pro Val Gln Trp Leu Thr Thr Gln Lys Gln Ala Ala Asp Lys
50                  55                          60

Val Val Phe Leu Leu Pro Ser Asp Val Pro Thr Leu Cys Asp Ser Ala
65              70                  75                      80

Cys Gly His Asn Glu Gly Ser Ala Arg Glu Asn Ser Gln Asp Leu Phe
                85                  90                  95

Pro Leu Ala Phe Asn Leu Phe Cys Ser Asp Phe Ser Gln Thr His
                100             105             110

Leu His Lys Tyr Leu Val Val Tyr Leu Gly Gly Ala Asp Leu Lys Gly
            115             120             125

Asp Tyr Asn Ala Leu Ser Val Cys Pro Gln Tyr His Leu Met Lys Asp
        130             135             140

Ala Thr Ala Phe His Thr Glu Leu Leu Lys Ala Thr Gln
145             150             155

<210> SEQ ID NO 30
<211> LENGTH: 157
<212> TYPE: PRT
<213> ORGANISM: Homo sapiens

<400> SEQUENCE: 30

Leu Leu Pro Pro Ile Lys Val Leu Val Val Tyr Pro Ser Glu Ile Cys
1               5                   10                  15

Phe His His Thr Ile Cys Tyr Phe Thr Glu Phe Leu Gln Asn His Cys
            20                  25                  30

Arg Ser Glu Val Ile Leu Glu Lys Trp Gln Lys Lys Ile Ala Glu
        35                  40                  45

Met Gly Pro Val Gln Trp Leu Ala Thr Gln Lys Lys Ala Ala Asp Lys
50                  55                          60

Val Val Phe Leu Leu Ser Asn Asp Val Asn Ser Val Cys Asp Gly Thr
65              70                  75                      80

Cys Gly Lys Ser Glu Gly Ser Pro Ser Glu Asn Ser Gln Asp Leu Phe
                85                  90                  95

Pro Leu Ala Phe Asn Leu Phe Cys Ser Asp Leu Arg Ser Gln Ile His
                100             105             110

Leu His Lys Tyr Val Val Val Tyr Phe Arg Glu Ile Asp Thr Lys Asp
            115             120             125

Asp Tyr Asn Ala Leu Ser Val Cys Pro Lys Tyr His Leu Met Lys Asp
        130             135             140

Ala Thr Ala Phe Cys Ala Glu Leu Leu His Val Lys Gln
145             150             155

<210> SEQ ID NO 31
<211> LENGTH: 176
<212> TYPE: PRT
<213> ORGANISM: Mus sp.

<400> SEQUENCE: 31

Arg Lys Val Trp Ile Val Tyr Ser Ala Asp His Pro Leu Tyr Val Glu
1               5                   10                  15
```

Val Val Leu Lys Phe Ala Gln Phe Leu Ile Thr Ala Cys Gly Thr Glu
            20                  25                  30

Val Ala Leu Asp Leu Leu Glu Glu Gln Val Ile Ser Glu Val Gly Val
        35                  40                  45

Met Thr Trp Val Ser Arg Gln Lys Gln Glu Met Val Glu Ser Asn Ser
    50                  55                  60

Lys Ile Ile Ile Leu Cys Ser Arg Gly Thr Gln Ala Lys Trp Lys Ala
65                  70                  75                  80

Ile Leu Gly Trp Ala Glu Pro Ala Val Gln Leu Arg Cys Asp His Trp
                85                  90                  95

Lys Pro Ala Gly Asp Leu Phe Thr Ala Ala Met Asn Met Ile Leu Pro
            100                 105                 110

Asp Phe Lys Arg Pro Ala Cys Phe Gly Thr Tyr Val Val Cys Tyr Phe
        115                 120                 125

Ser Gly Ile Cys Ser Glu Arg Asp Val Pro Asp Leu Phe Asn Ile Thr
    130                 135                 140

Ser Arg Tyr Pro Leu Met Asp Arg Phe Glu Glu Val Tyr Phe Arg Ile
145                 150                 155                 160

Gln Asp Leu Glu Met Phe Glu Pro Gly Arg Met His Arg Val Gly Glu
                165                 170                 175

<210> SEQ ID NO 32
<211> LENGTH: 175
<212> TYPE: PRT
<213> ORGANISM: Homo sapiens

<400> SEQUENCE: 32

Arg Lys Val Trp Ile Ile Tyr Ser Ala Asp His Pro Leu Tyr Val Asp
1               5                   10                  15

Val Val Leu Lys Phe Ala Gln Phe Leu Leu Thr Ala Cys Gly Thr Glu
            20                  25                  30

Val Ala Leu Asp Leu Leu Glu Glu Gln Ala Ile Ser Glu Ala Gly Val
        35                  40                  45

Met Thr Trp Val Gly Arg Gln Lys Gln Glu Met Val Glu Ser Asn Ser
    50                  55                  60

Lys Ile Ile Val Leu Cys Ser Arg Gly Thr Arg Ala Lys Trp Gln Ala
65                  70                  75                  80

Leu Leu Gly Arg Gly Ala Pro Val Arg Leu Arg Cys Asp His Gly Lys
                85                  90                  95

Pro Val Gly Asp Leu Phe Thr Ala Ala Met Asn Met Ile Leu Pro Asp
            100                 105                 110

Phe Lys Arg Pro Ala Cys Phe Gly Thr Tyr Val Val Cys Tyr Phe Ser
        115                 120                 125

Glu Val Ser Cys Asp Gly Asp Val Pro Asp Leu Phe Gly Ala Ala Pro
    130                 135                 140

Arg Tyr Pro Leu Met Asp Arg Phe Glu Glu Val Tyr Phe Arg Ile Gln
145                 150                 155                 160

Asp Leu Glu Met Phe Gln Pro Gly Arg Met His His Val Arg Glu
                165                 170                 175

<210> SEQ ID NO 33
<211> LENGTH: 169
<212> TYPE: PRT
<213> ORGANISM: Mus sp.

<400> SEQUENCE: 33

Gly Ser Arg Thr Ala Leu Leu His Ser Ala Asp Gly Ala Gly Tyr
1               5                   10                  15

Glu Arg Leu Val Gly Ala Leu Ala Ser Ala Leu Ser Gln Met Pro Leu
            20                  25                  30

Arg Val Ala Val Asp Leu Trp Ser Arg Glu Leu Ser Ala His Gly
        35                  40                  45

Ala Leu Ala Trp Phe His His Gln Arg Arg Ile Leu Gln Glu Gly
50                  55                  60

Gly Val Val Ile Leu Leu Phe Ser Pro Ala Val Ala Gln Cys Gln
65                  70                  75                  80

Gln Trp Leu Gln Leu Gln Thr Val Glu Pro Gly Pro His Asp Ala Leu
            85                  90                  95

Ala Ala Trp Leu Ser Cys Val Leu Pro Asp Phe Leu Gly Arg Ala
            100                 105                 110

Thr Gly Arg Tyr Val Gly Val Tyr Phe Asp Gly Leu Leu His Pro Asp
            115                 120                 125

Ser Val Pro Ser Pro Phe Arg Val Ala Pro Leu Phe Ser Leu Pro Thr
130                 135                 140

Gln Leu Pro Ala Phe Leu Asp Ala Leu Gln Gly Gly Cys Ser Thr Ser
145                 150                 155                 160

Ala Gly Arg Pro Ala Asp Arg Val Glu
            165

<210> SEQ ID NO 34
<211> LENGTH: 172
<212> TYPE: PRT
<213> ORGANISM: Homo sapiens

<400> SEQUENCE: 34

Arg Gly Arg Ala Ala Leu Leu Tyr Ser Ala Asp Asp Ser Gly Phe
1               5                   10                  15

Glu Arg Leu Val Gly Ala Leu Ala Ser Ala Leu Cys Gln Leu Pro Leu
            20                  25                  30

Arg Val Ala Val Asp Leu Trp Ser Arg Glu Leu Ser Ala Gln Gly
        35                  40                  45

Pro Val Ala Trp Phe His Ala Gln Arg Arg Gln Thr Leu Gln Glu Gly
50                  55                  60

Gly Val Val Val Leu Leu Phe Ser Pro Gly Ala Val Ala Leu Cys Ser
65                  70                  75                  80

Glu Trp Leu Gln Asp Gly Val Ser Gly Pro Ala His Gly Pro His
            85                  90                  95

Asp Ala Phe Arg Ala Ser Leu Ser Cys Val Leu Pro Asp Phe Leu Gln
            100                 105                 110

Gly Arg Ala Pro Gly Ser Tyr Val Gly Ala Cys Phe Asp Arg Leu Leu
            115                 120                 125

His Pro Asp Ala Val Pro Ala Leu Phe Arg Thr Val Pro Val Phe Thr
130                 135                 140

Leu Pro Ser Gln Leu Pro Asp Phe Leu Gly Ala Leu Gln Gln Pro Arg
145                 150                 155                 160

Ala Pro Arg Ser Gly Arg Leu Gln Glu Arg Ala Glu
            165                 170

<210> SEQ ID NO 35
<211> LENGTH: 151
<212> TYPE: PRT

<213> ORGANISM: Homo sapiens

<400> SEQUENCE: 35

Glu Glu Leu Arg Lys Val Phe Ile Thr Tyr Ser Met Asp Thr Ala Met
1               5                   10                  15

Glu Val Val Lys Phe Val Asn Phe Leu Leu Val Asn Gly Phe Gln Thr
            20                  25                  30

Ala Ile Asp Ile Phe Glu Asp Arg Ile Arg Gly Ile Asp Ile Ile Lys
        35                  40                  45

Trp Met Glu Arg Tyr Leu Arg Asp Lys Thr Val Met Ile Ile Val Ala
50                  55                  60

Ile Ser Pro Lys Tyr Lys Gln Asp Val Glu Gly Ala Glu Ser Gln Leu
65                  70                  75                  80

Asp Glu Asp Glu His Gly Leu His Thr Lys Tyr Ile His Arg Met Met
                85                  90                  95

Gln Ile Glu Phe Ile Lys Gln Gly Ser Met Asn Phe Arg Phe Ile Pro
            100                 105                 110

Val Leu Phe Pro Asn Ala Lys Lys Glu His Val Pro Thr Trp Leu Gln
        115                 120                 125

Asn Thr His Val Tyr Ser Trp Pro Lys Asn Lys Asn Ile Leu Leu
    130                 135                 140

Arg Leu Leu Arg Glu Glu Glu
145                 150

<210> SEQ ID NO 36
<211> LENGTH: 151
<212> TYPE: PRT
<213> ORGANISM: Mus sp.

<400> SEQUENCE: 36

Glu Glu Leu Arg Lys Val Phe Ile Thr Tyr Ser Met Asp Thr Ala Met
1               5                   10                  15

Glu Val Val Lys Phe Val Asn Phe Leu Leu Val Asn Gly Phe Gln Thr
            20                  25                  30

Ala Ile Asp Ile Phe Glu Asp Arg Ile Arg Gly Ile Asp Ile Ile Lys
        35                  40                  45

Trp Met Glu Arg Tyr Leu Arg Asp Lys Thr Val Met Ile Ile Val Ala
50                  55                  60

Ile Ser Pro Lys Tyr Lys Gln Asp Val Glu Gly Ala Glu Ser Gln Leu
65                  70                  75                  80

Asp Glu Asp Glu His Gly Leu His Thr Lys Tyr Ile His Arg Met Met
                85                  90                  95

Gln Ile Glu Phe Ile Ser Gln Gly Ser Met Asn Phe Arg Phe Ile Pro
            100                 105                 110

Val Leu Phe Pro Asn Ala Lys Lys Glu His Val Pro Thr Trp Leu Gln
        115                 120                 125

Asn Thr His Val Tyr Ser Trp Pro Lys Asn Lys Asn Ile Leu Leu
    130                 135                 140

Arg Leu Leu Arg Glu Glu Glu
145                 150

<210> SEQ ID NO 37
<211> LENGTH: 147
<212> TYPE: PRT
<213> ORGANISM: Homo sapiens

<400> SEQUENCE: 37

```
Arg Asn Val Arg Phe His Ala Phe Ile Ser Tyr Ser Glu His Asp Ser
1               5                   10                  15

Leu Trp Val Lys Asn Glu Leu Ile Pro Asn Leu Glu Lys Glu Asp Gly
                20                  25                  30

Ser Ile Leu Ile Cys Leu Tyr Glu Ser Tyr Phe Asp Pro Gly Lys Ser
            35                  40                  45

Ile Ser Glu Asn Ile Val Ser Phe Ile Glu Lys Ser Tyr Lys Ser Ile
        50                  55                  60

Phe Val Leu Ser Pro Asn Phe Val Gln Asn Glu Trp Cys His Tyr Glu
65                  70                  75                  80

Phe Tyr Phe Ala His His Asn Leu Phe His Glu Asn Ser Asp His Ile
                85                  90                  95

Ile Leu Ile Leu Leu Glu Pro Ile Pro Phe Tyr Cys Ile Pro Thr Arg
            100                 105                 110

Tyr His Lys Leu Lys Ala Leu Leu Glu Lys Lys Ala Tyr Leu Glu Trp
        115                 120                 125

Pro Lys Asp Arg Arg Lys Cys Gly Leu Phe Trp Ala Asn Leu Arg Ala
        130                 135                 140

Ala Ile Asn
145
```